US011143657B2

(12) United States Patent
Finkelstein et al.

(10) Patent No.: US 11,143,657 B2
(45) Date of Patent: Oct. 12, 2021

(54) TOPOGRAPHIC GENOTYPING FOR DETERMINING THE DIAGNOSIS, MALIGNANT POTENTIAL, AND BIOLOGIC BEHAVIOR OF PANCREATIC CYSTS AND RELATED CONDITIONS

(71) Applicant: Interpace Diagnostics Corporation, Parsippany, NJ (US)

(72) Inventors: Sydney David Finkelstein, Pittsburgh, PA (US); Patricia Swalsky, Pittsburgh, PA (US)

(73) Assignee: Interpace Diagnostics Corporation, Parsippany, NJ (US)

( * ) Notice: Subject to any disclaimer, the term of this patent is extended or adjusted under 35 U.S.C. 154(b) by 768 days.

(21) Appl. No.: 15/912,654

(22) Filed: Mar. 6, 2018

(65) Prior Publication Data
US 2019/0049452 A1 Feb. 14, 2019

Related U.S. Application Data

(63) Continuation of application No. 14/305,727, filed on Jun. 16, 2014, now abandoned, which is a continuation of application No. 11/255,978, filed on Oct. 24, 2005, now abandoned.

(60) Provisional application No. 60/679,969, filed on May 12, 2005, provisional application No. 60/679,968, filed on May 12, 2005, provisional application No. 60/644,568, filed on Jan. 19, 2005, provisional application No. 60/631,240, filed on Nov. 29, 2004, provisional application No. 60/620,926, filed on Oct. 22, 2004.

(51) Int. Cl.
| | |
|---|---|
| *G01N 33/574* | (2006.01) |
| *C12Q 1/6806* | (2018.01) |
| *C12Q 1/6827* | (2018.01) |
| *G16H 50/30* | (2018.01) |
| *C12Q 1/6886* | (2018.01) |

(52) U.S. Cl.
CPC ..... *G01N 33/57438* (2013.01); *C12Q 1/6806* (2013.01); *C12Q 1/6827* (2013.01); *C12Q 1/6886* (2013.01); *G16H 50/30* (2018.01); *C12Q 2600/106* (2013.01); *C12Q 2600/112* (2013.01); *C12Q 2600/118* (2013.01); *C12Q 2600/154* (2013.01); *C12Q 2600/156* (2013.01)

(58) Field of Classification Search
None
See application file for complete search history.

(56) References Cited

U.S. PATENT DOCUMENTS

| | | |
|---|---|---|
| 5,188,964 A | 2/1993 | McGuire et al. |
| 5,320,840 A | 6/1994 | Camble et al. |
| 5,380,645 A | 1/1995 | Vogelstein |
| 5,491,062 A | 2/1996 | McKenzie et al. |
| 5,580,728 A | 12/1996 | Perlin |
| 5,670,325 A | 9/1997 | Lapidus et al. |
| 5,830,711 A | 11/1998 | Barany et al. |
| 5,843,644 A | 12/1998 | Liotta et al. |
| 6,143,529 A | 11/2000 | Lapidus et al. |
| 6,300,077 B1 | 10/2001 | Shuber et al. |
| 6,340,563 B1 | 1/2002 | Finkelstein et al. |
| 6,428,964 B1 | 8/2002 | Shuber |
| 6,465,177 B1 | 10/2002 | Hoon |
| 6,750,020 B2 | 6/2004 | Shuber |
| 6,919,174 B1 | 7/2005 | Shuber |
| 7,014,999 B2 | 3/2006 | Finkelstein et al. |
| 2001/0034038 A1 | 10/2001 | Hung |
| 2003/0165895 A1 | 9/2003 | Czerniak et al. |
| 2006/0088871 A1 | 4/2006 | Finkelstein et al. |
| 2006/0115844 A1 | 6/2006 | Finkelstein et al. |
| 2006/0141497 A1 | 6/2006 | Finkelstein et al. |
| 2006/0154274 A1 | 7/2006 | Finkelstein et al. |
| 2011/0008914 A1 | 1/2011 | Yeung et al. |

FOREIGN PATENT DOCUMENTS

| | | |
|---|---|---|
| EP | 0671473 A1 | 9/1995 |
| WO | 9419492 A1 | 9/1994 |
| WO | 199854364 A1 | 12/1998 |
| WO | 199910528 A1 | 3/1999 |
| WO | 02086448 A2 | 10/2002 |
| WO | 2006047481 A2 | 5/2006 |

OTHER PUBLICATIONS

Apple et al. Immunohistochemical Evaluation of K-ras, p53, and HER-2/neu Expression in Hyperplastic, Dysplastic, and Carcinomatous Lesions of the Pancreas: Evidence for Multistep Carcinogenesis Human Pathology vol. 30, pp. 123-129 (Year: 1999).*
Boot et al., "Validity of carcinoembryonic antigen and carbohydrate antigen 19-9 measurements in pancreatic cyst fluid with a serum-based immunoassay," Clinical Chemistry (2010) 56(8):1351-1352.
Brugge et al., "Diagnosis of pancreatic cystic neoplasms: a report of the cooperative pancreatic cyst study," (2004) 126(5):1330-1336.
Khalid et al., "ACG practice guidelines for the diagnosis and management of neoplastic pancreatic cysts," Am J Gastroenterol (2007) 102(10):2339-2349.
http://www.salimetrics.com/assets/documents/Spit.sub.-Tips.sub.-.sub.-Inter.sub.-Intra.sub.-Assay.sub.-Coefficients.sub.-of.sub.-Variability.pdf.

(Continued)

*Primary Examiner* — John S Brusca
(74) *Attorney, Agent, or Firm* — Troutman Pepper Hamilton Sanders LLP

(57) ABSTRACT

The application relates to a method of a predicting the presence of invasive pancreatic cancer or high grade dysplasia, pre-cancerous pancreatic states and non-neoplastic conditions comprising detailed molecular analysis incorporating DNA quality and quantity, K-ras mutational analysis and a broad spectrum of tumor suppressor gene linked microsatellite LOH. Methods of diagnosing, determining prognosis of and determining a course of treatment for pancreatic cancer or high grade dysplasia, pre-cancerous pancreatic states and non-neoplastic conditions are also provided.

20 Claims, 5 Drawing Sheets

(56) References Cited

OTHER PUBLICATIONS

Pitman, M. et al., "Pancreatic cysts preoperative diagnosis and clinical management", Cancer Cytopathology, (2010) p. 1-13.
Non-final Office Action dated Jan. 10, 2018 in U.S. Appl. No. 15/147,960.
Leob "A Mutator Phenotyp in Cancer", Cancer Research (2001) 61,3230-3239.
Heng et al., "Cancer progression by non-clonal chromosome aberrations." Jornal of Cellular Biochemistry (2006) 98:1424-1435.
Grizzi et al., "Cancer: looking for simplicity and finding complexity." Cancer Cell International (2006) 6:4 pp. 1-7.
Glazier "An Inconvenient Truth: Cancer is a hugely diverse, complex, unpredictable, non-linear, stochastic evolutionary w process." retrieved Sep. 16, 2009 from http://www. cu re can cerp ro ject.o rg/beta/pdf I An %201 n co nve n ie nt%20T ruth, %20Ca nee r%20 is%20a %20 huge ly%20d ive rse%20co mplex%20stochastic% 20evolutionary%20process.pdf (2009).
Sieben et al. "PCR Artifacts in LOH and MSI Analysis of Microdissected Tumor Cells" Jan. 2000, Human Pathology, 31: 1414-1419.
Skotheim et al. "Evaluation of Loss of Heterozygosity/ Allelic Imbalance Scoring in Tumor DNA" May 2001, Cancer Genetics and Cytogenetics, 127(1):64-70.
Bluteau et al. "Semi-automated Quantitative Method for Detecting the Loss of Heterozygosity at Chromosome 4 in Hepatocellular Carcinoma" Nov. 1999, Biosis.
Anderson et al. Intrachromosomal Genomic Instability in Human Sporadic Colorectal Cancer Measured by Genome-Wide Allelotyping and Inter-(Simple Sequence Repeat) PCR, Nov. 2001, Cancer Research 61(22):8274-8283.
Gall et al., "DNA Amplification by polymerase chain reaction from brain tissues embedded in paraffin," Int. J. Exp. Path. (1993) 74, DD 333-397.
Hodges et al., "Expanded TcR Vb5 1 family in a high-grade B cell immunoblastic lymphoma," Leukimia (1995), vol. 9, pp. 1108-1112, Nature Publishing Group, London, England.
Saiki, "Chapter I, The Design and Optimization of the PCR," PCR Technology. Principles and applications for DNA amplification, New York, Stockton Press, 1989, DD 7-16.
Hodges et al., "Modification of IgH PCR clonal analysis by the addition of sucrose and cresol red directly to PCR reaction mixes," Clinical Pathology: Molecular Pathology, 1997; vol. 50, pp. 164-166, Molecular Immunology Group, Southampton, UK.
Dixon et al., "Expression profiling of single cells using 3 prime end amplification (TPEA) PCR," Nucleic Acids Research, 1998, vol. 26, No. 19, PD 4426-4431, Oxford University Press, Oxford, England.
Warren et al., "Drad21, a *Drosophila* rad2 I homologue expressed in S-phase cells," Gene 250 (2000) p. 77-84, Elsevier, London England.
Husain, "Complex expression of natural killer receptor genes in single natural killer cells," Immunology 2002, vol. 106, DD 373-380, Blackwell Science Ltd., Oxford, England.
Wistuba et al., "Sequential molecular abnormalities are involved in the multistage development of squamous cell lung carcinoma," Oncogene (1999), vol. 18, pp. 643-650, Nature Publishing Group, [Basingstoke, England.
Wistuba et al., "Allelic Losses at Chromosome 8p2 I-23 are Early and Frequent Events in the Pathogenesis of Cancer," Cancer Research, vol. 59, (1999), pp. 1973-1979, American Association for Cancer !Research, Baltimore, MD.
Daido, S. et al., "Loss of heterozygosity on chromosome IOq associated with malignancy ad prognosis in astrocytic tumors, and discovery of novel loss regions," Oncology Reports (2004), vol. 12, pp. 789-795, National Hellenic Research Foundation, Athens, Greece.
Ohtsu et al., "Clinical Investigation of Neuroblastoma with Partial Deletion in the Short Arm of Chromosome I," Clinical Cancer Research, vol. 3, pp. 1221-1228, Jul. 1997.

Loupart et al., "Allelic Imbalance on Chromosome I in Human Breast Cancer. I. Minisatellite and RFLP Analysis," Genes, Chromosomes & Cancer, (1995) vol. 12, pp. 16-23, Wiley-Liss, Inc., New York, New York.
Yeh et al., "Frequent Genetic Alterations at the Distal Region of Chromosome Ip in Human Hepatocelular Carcinomas," Cancer Research, vol. 54, pp. 4188-4192, Aug. 1, 1994, American Association for Cancer Research, Baltimore, MD.
Thompson et al., "Loss of Heterozygosity in Chromosome 14q in Neuroblastoma," Medical and Pediatric Oncology, vol. 36, DP 28-31 (2001) Wiley-Liss, Inc., New York, New York.
Hung, "Allele-Specific Chromosome 3p Deletions Occur at an Early Stage in the Pathogenesis of Lung Carcinoma," JAMA 1995, vol. 273, pp. 558-563, American Medical Association, Chicago, IL.
Husman et al., "Processing of long-stored archival cervical smears for human papillomavirus detection by the polymerase chain reaction," British Journal of Cancer ( 1995) 72, pp. 412-417 University College London, London, United Kingdom.
Ben-Ezra et al., "Effect of Fixation on the Amplification of Nucleic Acids from Paraffin-embedded Material by the polymerase Chain Reaction," The Journal of Histochemistry and Cytochemistry, 39(3), pp. 351-354 ( 1991) The Histochemical Society, Inc., Seattle, Washington.
Rogers, et al., "Analysis of DNA in Fresh and Fixed Tissue by the Polymerase Chain Reaction," American Journal of Pathology, vol. 136, No. 3, Mar. 1990, pp. 541-548, The American Society for Investigative Pathology, Bethesda, Maryland.
De Giorgi et al., "Formalin-induced infidelity in PCR-amplified DNA fragments," Molecular and Cellular Probes (1994) 8, pp. 459-462, Reed Elsevier Group, London, United Kingdom.
Williams, et al., "A High Frequency of Sequence Alterations is Due to Formalin Fixation of Archival Specimens," American Journal of Pathology, vol. 155, No. 5, (Nov. 1999), pp. 1467-1471, The American Society for Investigative Pathology, Bethesda, Maryland.
Wong, et al., "Mutations in BRCAI from Fixed, Paraffin-Embedded Tissue Can Be Artifacts of Preservation," Cancer Genet. Cytogenet. I 07, pp. 21-27 ( 1998), Reed Elsevier Group, London, United Kingdom.
Miller, et al., "Assessing Allelic Dropout and Genotype Reliability Using Maximum Likelihood," Genetics 160, (Jan. 2002), pp. 357-366, Genetics Society of America, Bethesda, Maryland.
Finkelstein SD, et al., "'Genotypic classification of colorectal adenocarcinoma. Biologica behavior correlates with K-ras-2 mutation type.'," Cancer (1993), vol. 71 (No. 12), p. 3827-3838, American Cancer Society, Atlanta, Georgia.
Finkelstein et al., "'Kras-2 topographic genotyping of pancreatic adenocarcinoma.'," Arch. Surg., vol. 129 (No. 4), p. 367-372, (Apr. 1, 1994), The American Medical Association, Chicago, Illinois.
Florell M.D., "Preservation of RNA for Funcational Genomic Studies: a Multidisciplinary Tumor Bank Protocol," The United States and Canadian Academy of Pathology, Inc., vol. 14, No. 2, pp. 116-128 (2001), Augusta, Georgia.
Tully, et al., "Analysis of 6 VNTR loci by 'multiplex' PCR and automated fluorescent detection," Human Genetics (1993) 92, pp. 554-562, Springer Berlin Heidelberg, Germany.
Gura "Antisense Has Growing Pains," Science, 270, pp. 575-577, (1995) Amer. Assn. For the Advancement of Science, Washington, D.C.
Innis et al. PCR Protocols. Adademic Press, Inc. pp. 3-12, 153-158, 348-355, 1990, Reed Elsevier Group, London, United Kingdom.
Rae, et al., "Genotyping for polymorphic druge metabolizing enzymes from paraffin-embedded and immunohistochemically stained tumor samples," Pharmacogenetics 2003, vol. 13, No. 8, pp. 501-507, Chapman & Hall, London, United Kingdom.
Gillespie, et al., "Evaluation of Non-Formalin Tissue Fixation for Molecular Profiling Studies," American Journal of Pathology, vol. 160, No. 2, (Feb. 2002), pp. 449-457, American Society for Investigative Pathology, Bethesda, Maryland.
Bernstein et al., "Comparison of Techniques for the Successful Detection of BRCAI Mutations in Fixed Paraffin-Embedded Tissue," Cancer Epidemiology, Biomarkers and Prevention, vol. 11, (Sep. 2002), pp. 809-811, American Association for Cancer Research, Philadelphia, Pennsylvania.

(56) References Cited

OTHER PUBLICATIONS

Dressen, et al., "Allelic Dropout Caused by Allele-Specific Amplification Failure in Single-Cell PCR of the Cystic Fibrosis .Delta. F508 Delection," Journal of Assisted Reproduction and Genetics, vol. 13, No. 2, 1996, pp. 112-114, Kluwer Academic/Plenum Publishers, New York, New York.

Forsthoefel, M.D., et al., "Optimization of DNA Extraction from Formalin-Fixed Tissue and Its Clinical Application in Duchenne Muscular Dystrophy," Anatomic Pathology, A.J.C.P, Jul. 1992, pp. 98-104, AASCP Press, Chicago, Illinois.

Küppers et al. "Tracing B cell development in human germinal centres by molecular analysis of single cells picked from histological sections", EMBO J. vol. 12, No. 13, pp. 4955-4967, 1993, Oxford University Press, Oxford, England.

Dressler, et al., "Policy guidelines for the utilization of formalin-fixed, paraffin-embedded tissue sections: the UNC SPORE experience," Breast Cancer Research and Treatment 58, pp. 31-39 (1999), Kluwer Academic Publishers, Netherlands.

Burton, et al., "Comparisoon of Histologic Stains for Use in PCR Analysis of Microdissected, Paraffin-Embedded Tissues," BioTechniques, vol. 24, No. I, pp. 86-91 (1998), Eaton Pub. Co., Natick, Massachusetts.

Meltzer et al. Reduction to homozygosity involving p53 in esophageal cancers demonstrated by PCR. PNAS, vol. 88, pp. 4976-4980, Jun. 1991, National Academy of Sciences, Washington, D.C.

Orkin et al., Report and Recommendations of the Panel to Assess the NIH Investment in Research on Gene Therapy ( 1995), NIH, Bethesda, Maryland.

Oud et al., "Extraction of Nuclei From Selected Regions in Paraffin-Embedded Tissue.sup.1,2," Cytometry, 7, pp. 595-600 (1986) Alan R. Liss, Inc., New York, New York.

Wiegand, et al., "DNA degradation in formalin fixed tissues," Pathologe, Nov. 1996; 17(6); 451-7, Springer-Verlag., Berlin, Germany (abstract in English).

Coates, et al., "Simplified procedures for applying the polymerase chain reaction to routinely fixed paraffin wax sections," Journal of Clinical Pathology 1991, 44, pp. 115-118, BMJ Pub. Group, London, United Kingdom.

Pretlow et al. "K-ras mutation in putative preneoplastic lesions in human colon". J. of Natl. Cancer Institute, vol. 85, No. 24, pp. 2004-2007, Dec. 1993, NIH, Bethesda, Maryland.

Reineke M. et al., "'p53 mutations in human adrenocortical neoplasms: immunohistochemical and molecular studies.'," J. Clin Endocrinol. and Metab. (1994), vol. 78 (No. 3), p. 790-794, Endocrine Society, Chevy Chase, Maryland.

Kösel et al., "Use of neuropathological tissue for molecular genetic studies: parameters affecting DNA extraction and polymerase chain reaction," Acta Neuropathol. (1994) 88, pp. 19-25, Springer Verlag, Berlin, Germany.

An, et al., "Removal ofinhibitor(s) of the polymerase chain reaction from formalin fixed, paraffin wax embedded tissues," Journal of Clinical Pathology 1991, 44 pp. 924-927, BMJ Pub. Group, London, United Kingdom.

Sen et al., "Microdissected Double-Minute DNA Detects Variable Patterns of Chromosomal Localizations and Multiple Abundantly Expressed Transcripts In Normal and Leukemic Cells," Genomics, 19(3), pp. 542-551 (1994) Academic Press, Inc., San Diego, California.

Shibata et al. "Specific Genetic Analysis of microscopic tissue after selective ultraviolet radiation fraction and the PCR", Am. J. of Pathology, vol. 121, No. 3, pp. 539-543, Sep. 1992, The American Society for Investigative Pathology, Bethesda, Maryland.

Slebos, RJC, et al., "'K-ras oncogene activation as a prognostic marker in adenocarcinoma of the lung.'," New Engl. J. Med. ( 1990), vol. 323 (No. 9), p. 561-565, Massachusetts Medical Society, Boston, Massachusetts.

Stenersen et al., "The selection of thin epithelial layers: a method for single cell preparations of very small biopsies from the vocal cords," Analytical Cellular Pathology, 2, pp. 253-258, (1990) Elsevier Science Publishers B.V., Amsterdam, Holland.

Goetz, et al., "Purification of DNA from Formaldehyde Fixed and Paraffin Embedded Human Tissue," Biochemical and Biophysical Research Communications, vol. 130, No. 1, 1985, pp. 118-126, Academic Press, New York, New York.

Murase M.D., et al., "Influence of Histochemical and Immunohistochemical Stains on Polymerase Chain Reaction," Modern Pathology, an official journal of the United States and Canadian Academy of Pathology, Inc., vol. 13, No. 2, oo. 14 7-151 (2000), Williams & Wilkins, Baltimore, Maryland.

Talmadge, "The pharmaceutics and delivery of therapeutic polypeptides and proteins," Advanced Drug Delivery Reviews, IO, pp. 247-299 (1993) Elsevier Science Publishers B.V., Amsterdam, Holland.

Teramoto et al. "Application of PCR to the microscopically identified cells on the slides" Acta Med. Okayama, vol. 48, No. 4, pp. 189-193, 1994, Okayama University Medical School, Okayama, Japan.

Lamballerie, et al., "Improved current methods for amplification of DNA from routinely processed liver tissue by PCR," Journal of Clinical Pathology 1994, 47, pp. 466-467, BMJ Pub. Group, London, United Kingdom.

Khalid A et al., "Free floating DNA mutational allelotyping ofEUS guided aspirates of pancreatic cysts is predictive of underlying biological behavior: Preliminary data on a novel techniquec." Pancreas, vol. 27, No. 4, Nov. 2003, p. 391, The American Pancreatic Association; Chicago, Illinois.

Khalid A et al., "Mutational Allelotyping of Aspirated Free-Floating DNA Predicts the Biological Behavior of Cystic Pancreatic Neoplasms" Gastrointestinal Endoscopy, vol. 59, No. 5, Apr. 2004, Elsevier, Netherlands.

Hruban RH et al., "genetic progression in the pancreatic ducts." The American Journal of Pathology, vol. 156, No. 6, Jun. 2000, pp. 1821-1825, The American Society for Investigative Pathology, Bethesda, Maryland.

Khalid A et al., "Molecular diagnosis of solid and cystic lesions of the pancreas" Gastroenterology Clinics of North America, vol. 33, No. 4, 2004, p. 891-906, W.B. Saunders Co., Philadelphia, Pennsylvania.

Khalid A et al., "The Role of Pancreatic Cyst Fluid Molecular Analysis in Predicting Cyst Pathology" Clinical Gastroenterology and Hepatology, vol. 3, No. 10, p. 967-973, Oct. 2005, American Gastroenterological Association, Philadelphia, Pennsylvania.

Khalid A et al., "First hit K-ras point mutation followed by tumor suppressor gene allelic loss predicts malignancy in EUS guided pancreatic cyst aspirate." Pancreas, vol. 29, No. 4, Nov. 2004 p. 357, Annual Meeting of the American Pancreatic Association; Chicago, Illiniois.

Khalid A et al., "Comparison of EUS guided pancreatic Cyst (PC) Aspirate Cea, DNA Quantity and Quality: Mutational Acquisition Pattern in Predicting Malignancy." Gastrointestinal Endoscopy, vol. 61, No. 5, Apr. 2005. Elsevier, Netherlands.

Isaacs et al., "Detection of LOH and mitochondrial DNA alterations in ductal lavage and nipple aspirate fluids from high-risk patients," Breast Cancer Research and Treatment, vol. 84, No. 2, Mar. 2004, pp. 99-105.

Liloglou Triantafillos et al., "Cancer-specific Genomic Instability in Bronchial Lavage: A Molecular Tool for Lung Cancer Detection," Cancer Research, vol. 61, No. 4, Feb. 15, 2001, DD. 1624-1628.

Pricolo et al., "Prognostic Value of TP53 and K-ras-2 Mutational Analysis in Stage III Carcinoma of the Colon," American Journal of Surgery, vol. 171, No. 1, Jan. 1996, pp. 41-46.

Minamoto et al., "K-ras Mutation: Early Detection in Molecular Diagnosis and Risk Assessment of Colorectal, Pancreas, and Lung Cancers—A Review," Cancer Detection and Prevention, vol. 24, No. I, 2000, DD. I-.

Evron et al., "Detection of breast cancer cells in ductal lavage fluid by methylatiorrspecific PCR," The Lancet, vol. 357, No. 9265, Apr. 28, 2001, pp. 1335-1336.

Sasatomi et al., "Comparison of Accumulated Allele Loss between Primary Tumor and Lymph Node Metastasis in Stage II Non-small Cell Lung Carcinoma: Implications for the Timing of Lymph Node Metastasis and Prognostic Value," Cancer Research, vol. 62, No. 9, May 1, 2002, DD. 2681-2689.

(56) References Cited

OTHER PUBLICATIONS

NonFinal Office Action dated Apr. 1, 2008, in U.S. Appl. No. 11/256,150.
Official Action dated Dec. 18, 2007 by the European Patent Office in European Application No. 05818189.2.
Notice of Allowance dated Jun. 3, 2019, in U.S. Appl. No. 15/147,960.
NonFinal Office Action dated Nov. 14, 2018, in U.S. Appl. No. 15/147,960.

* cited by examiner

FIG. 2

IMPORTANCE OF TIMING OF MUTATION ACQUISITION

- The timing of mutation acquisition plays a role in treatment responsiveness (clonal expansion)
- Early acquisition of 1p/19q loss will delineate the treatment responsive subset since it will result in all glioma cells possessing this potentially favorable alteration
- Later acquisition of 1p/19q would not be as favorable since precursor cells without 1p/19q loss will be present to resist and grow in the face of treatment

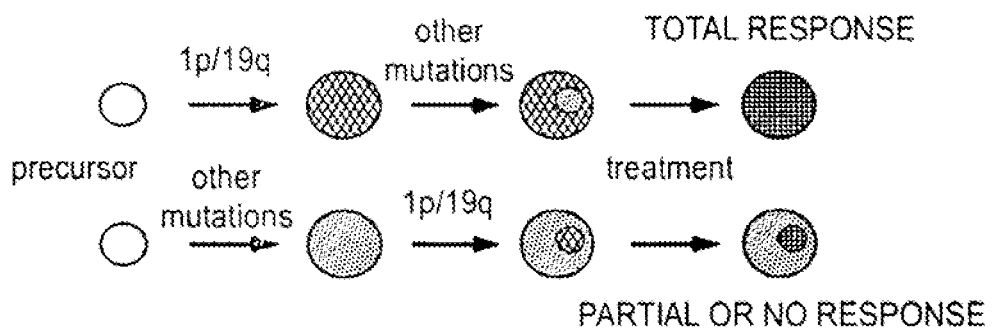

TWO CLONES IDENTIFIED DERIVED FROM PRECURSOR
WITH 17p13 ALLELIC IMBALANCE

TOPOGRAPHIC GENOTYPING FOR DETERMINING THE DIAGNOSIS, MALIGNANT POTENTIAL, AND BIOLOGIC BEHAVIOR OF PANCREATIC CYSTS AND RELATED CONDITIONS

REFERENCE TO RELATED APPLICATIONS

This application claims benefit of U.S. Provisional Application Nos. 60/620,926 filed Oct. 22, 2004, 60/631,240 filed Nov. 29, 2004, 60/644,568 filed Jan. 19, 2005, 60/679,968 filed May 12, 2005, and 60/679,969 filed May 12, 2005 which are incorporated herein in their entirety for all purposes.

FIELD OF THE INVENTION

The application relates to a method of a predicting the presence of invasive pancreatic cancer, high grade dysplasia, pre-cancerous pancreatic states and alternative neoplastic and non-neoplastic conditions comprising detailed molecular analysis incorporating DNA quality and quantity, K-ras mutational analysis, and a broad spectrum of tumor suppressor gene linked microsatellite loss of heterozygosity. The application provides a means to clearly separate cancer from non-cancer states such as those produced by inflammation, infection and trauma involving the pancreas. Methods of diagnosing, determining prognosis of, and determining a course of treatment for pancreatic cancer or high grade dysplasia, pre-cancerous pancreatic states, and non-neoplastic conditions are also provided.

BACKGROUND OF THE INVENTION

Pancreas cancer is invariably fatal with less than 5% survival beyond five years for patients currently diagnosed with the disease. While better chemotherapy agents to treat the disease already present are needed, the emphasis has turned towards early detection of pancreatic cancer in order to recognize the disease in its early stages or pre-cancer stages. Success has been achieved in part by the availability of minimally invasive technologies and equipment such as endoscopic ultrasound and fine needle biopsy aspiration. The rate limiting step for early detection of pancreatic cancer is now recognized as the pathology examination of tissue and fluid samples. The pathology examination of tissue and fluid has not changed substantially for over half a century. Pathology evaluation takes the form of microscopic examination of such specimens with an indeterminate diagnosis rate of over 50% and an inability to reliably define microscopic criteria for early pancreatic cancer that can distinguish between similar appearing neoplastic and non-neoplastic lesions.

Most commonly, the early changes of pancreatic cancer are pancreatic cysts. However, not every pancreatic cyst is necessarily early pancreatic cancer. As pancreatic imaging improves, the need to definitively diagnose pancreatic cysts increases.

Pancreatic cysts are being detected with increasing frequency due to the wide spread use of high quality imaging tests. The majority of these are cysts are mucinous cystic neoplasms (MCN) (Fernandez-del Castillo, et al., *Arch. Surg.* 2003 138(4): 427-33). MCN are considered premalignant, and encompass intraductal pancreatic mucinous neoplasia (IPMN) and mucinous cystadenomas (MCA). The natural history of MCN is unknown, and the frequency and timing of malignant change is unclear. However, tools to differentiate malignant cysts from pre-malignant cysts on diagnostic needle aspiration or biopsy specimens currently do not exist.

Current methods to evaluate pancreatic cysts employ imaging and cyst aspirate analysis. In the absence of an associated mass representing advanced and frequently incurable disease, there are no reliable radiological criteria to separate these categories. Endoscopic ultrasound (EUS) is thought to be the most sensitive test to evaluate the pancreas. However, recent studies of this technique of differentiating malignant from pre-malignant pancreatic cysts have been disappointing. Unless the cyst is already advanced, there are no reliable EUS features for a malignant pancreatic cyst (Ahmad, et. al., *Gastrointest. Endosc.* 2003 58(1): 59-64; and Brugge, et al., *Gastroenterology* 2004 126(5): 1330-6). While early pancreatic cancer cannot be reliably diagnosed solely by EUS, the latter provides an ideal means to secure a representative specimen sample with which pathology can attempt a definitive diagnosis.

The sensitivity of cytological analysis of the pancreatic cyst aspirate usually performed under EUS guidance is suboptimal, due to the acellular or paucicellular nature of the aspirate, i.e., few cells are found in the aspirate upon which pathology analysis can be performed and the few cells that are available for microscopic analysis manifest indeterminate morphologic features. Aspirate carcinoembryonic antigen (CEA) levels are considered to be the most reliable indicator of a cyst of mucinous origin. However, the results provide no information as to the presence of cancer (Brugge, et al., 2004).

SUMMARY OF THE INVENTION

The invention described here introduces novel methods, reagents and scientific approaches not previously reported to significantly improve the analysis of pancreatic cyst fluid specimens. The invention also provides for enhancing a definitive diagnosis and prediction of early pancreatic cancer, and clearly separating this from the diagnosis of similar appearing but distinct pancreatic abnormalities and pre-cancerous conditions.

In one embodiment, the present invention provides a method for predicting the presence of a pancreatic anomaly in a patient suffering from pancreatic cysts comprising:
  a) performing molecular analysis of DNA from an aspirate from a patient pancreatic cyst comprising:
    i) performing an optical density analysis of the aspirate to determine DNA quantity;
    ii) performing a quantitative PCR analysis of the aspirate to determine DNA quality;
    iii) performing competitive template PCR to determine DNA quality; and
  b) performing mutation analysis of the DNA in the aspirate comprising:
    (i) determining the presence of mutations in a tumor suppressor gene and/or the presence of a cancer related genetic marker;
    (ii) determining tumor suppressor gene loss of heterozygosity (LOH) by analyzing polymorphic microsatellites or other polymorphic markers linked to tumor suppressor genes with respect to their allelic balance;
    (iii) determining point mutations in the K-ras oncogene and/or point mutations in at least one other cancer-associated gene;

(iv) determining other structural alterations in DNA (gene amplification, gene translocation or rearrangement, or epigenetic modification of DNA by DNA methylation);

(v) determining the percentage of mutated DNA from steps b)(ii) and b)(iii); and (vi) determining the specific temporal sequence of mutation accumulation based on step (v); wherein the temporal sequence of mutation accumulation is predictive of the presence of a pancreatic anomaly.

The method may further comprise confirming the results of steps a) and b) by comparing said results with a pathologic analysis of a cystic lesion surgically obtained from the patient. The method may also further comprise analyzing the cyst carcinoembryonic antigen (CEA) level of the aspirate. Preferably, the DNA in the aspirate is free-floating or free and adherent to the surface of cells or tissue constituents of the cyst.

Preferably, the cycles of quantitative PCR performed in step a)(ii) is greater than a threshold unique for that specific type of DNA. Preferably, the cycles of quantitative PCR performed in step a)(ii) is greater than 30. More preferably, the cycles of quantitative PCR performed in step a)(ii) is 29 to 30. Most preferably, the cycles of quantitative PCR performed in step a)(ii) is less than or equal to 29.

Preferably, the optical density is about 2.0 to about 7.5 (i.e., representing the allele ration). More preferably, the optical density is about 7.5 or higher. Preferably, the allele ratio is two standard deviations beyond the average for the ratio of the specific pairing of polymorphic alleles.

Preferably, the patient is a mammal. More preferably, the patient is a human.

The pancreatic anomaly may be a pancreatic cancer or dysplasia, pre-cancerous pancreatic state, or non-neoplastic condition. The pancreatic cancer or dysplasia may be pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma). The pre-cancerous pancreatic state may be mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may be pancreatitis, pancreatic pseudocyst, mesothelial cyst, lymphoepithelial cyst of the pancreas, and ischemic necrosis of the pancreas.

In a further embodiment, the present invention provides a method for diagnosing and/or determining the prognosis of a pancreatic anomaly in a patient suffering from pancreatic cysts comprising:

a) performing molecular analysis of DNA from an aspirate from a patient pancreatic cyst comprising:
  (i) performing an optical density analysis of the aspirate to determine DNA quantity;
  (ii) performing a quantitative PCR analysis of the aspirate to determine DNA quality;
  (iii) performing competitive template PCR to determine DNA quality; and b) performing mutation analysis of the DNA in the aspirate comprising:
  (i) determining the presence of one or more mutations in a tumor suppressor gene and/or the presence of a cancer related genetic marker;
  (ii) determining tumor suppressor gene loss of heterozygosity (LOH) by analyzing polymorphic microsatellites or other polymorphic markers linked to tumor suppressor genes with respect to their allelic balances;
  (iii) determining point mutations in the K-ras oncogene and/or point mutations in at least one other cancer-associated gene;
  (iv) determining other structural alterations in DNA;
  (v) determining the percentage of mutated DNA from steps b)(ii) and b)(iii); and
  (vi) determining the specific temporal sequence of mutation accumulation based on step v), and diagnosing and/or determining the prognosis of a pancreatic anomaly of the patient in need based on the results of steps a) and b).

The pancreatic anomaly may be a pancreatic cancer or dysplasia, pre-cancerous pancreatic state, or non-neoplastic condition. The pancreatic cancer or dysplasia may be pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholanglocarcinoma). The pre-cancerous pancreatic state may be mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may be pancreatitis, pancreatic pseudocyst, mesothelial cyst, lymphoepithelial cyst of the pancreas, and ischemic necrosis of the pancreas.

In yet a further embodiment, the present invention provides a method for determining a course of treatment for a pancreatic anomaly in a patient suffering from pancreatic cysts comprising:

a) performing molecular analysis of DNA from an aspirate from a patient pancreatic cyst comprising:
  (i) performing an optical density analysis of the aspirate to determine DNA quantity;
  (ii) performing a quantitative PCR analysis of the aspirate to determine DNA quality;
  (iii) performing competitive template PCR to determine DNA quality; and b) performing mutation analysis of the DNA in the aspirate comprising:
  (i) determining the presence of mutations in a tumor suppressor gene and/or the presence of a cancer related genetic marker;
  (ii) determining tumor suppressor gene loss of heterozygosity (LOH) by catalyzing polymorphic microsatellites or other polymorphic markers linked to tumor suppressor genes with respect to their allelic balances;
  (iii) determining point mutations in the K-ras oncogene and/or point mutations in at least one other cancer-associated gene;
  (iv) determining other structural alterations in DNA;
  (v) determining the percentage of mutated DNA from steps b)(ii) and b)(iii); and
  (vi) determining the specific temporal sequence of mutation accumulation based on step v), wherein the results of steps a) and b) are used to determine a course of therapy for a patient suffering from a pancreatic anomaly.

The pancreatic anomaly may be a pancreatic cancer or dysplasia, pre-cancerous pancreatic state, or non-neoplastic condition. The pancreatic cancer or dysplasia may be pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma). The pre-cancerous pancreatic state may be mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may be pancreatitis, pancreatic pseudocyst, mesothelial cyst, lymphoepithelial cyst of the pancreas, and ischemic necrosis of the pancreas.

BRIEF DESCRIPTION OF DRAWINGS

FIG. 2. Schematic of Acquisition and Treatment Responsiveness.

DETAILED DESCRIPTION OF THE INVENTION

Figure 1A:
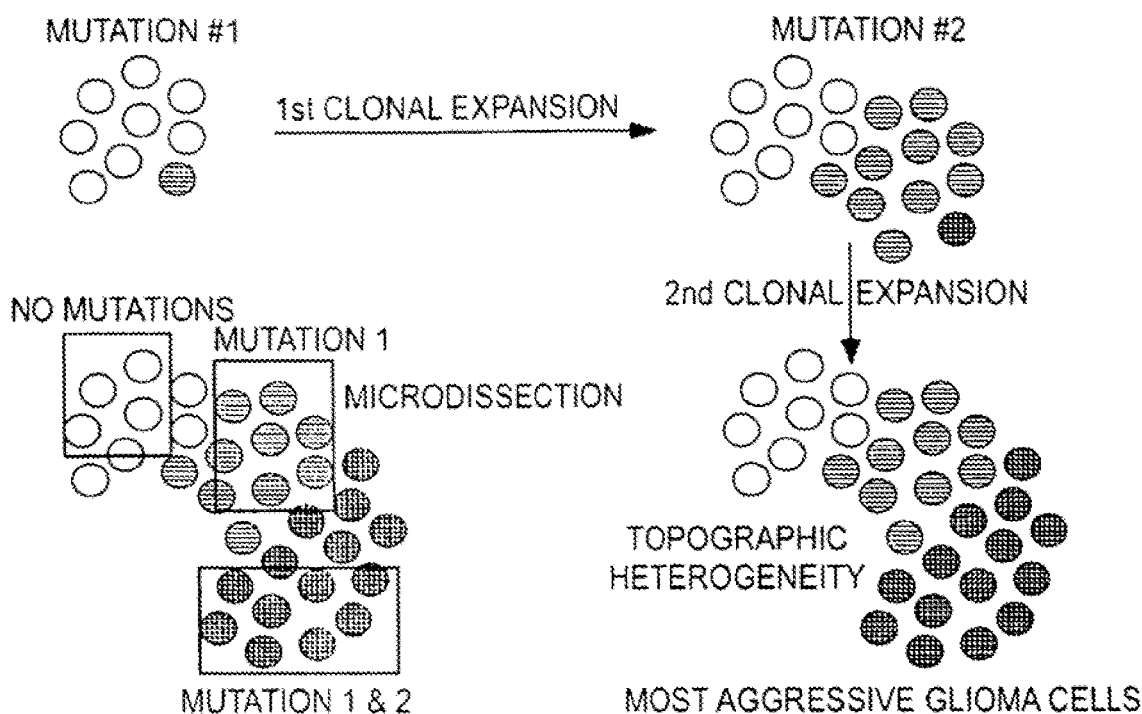
FIGS. 1A and B. Schematic of microdissection genotyping.

Without wishing to be bound by theory, it is believed that pancreatic conditions of a non-neoplastic cause, such as pancreatic pseudocyst resulting from trauma (as one example but not limited to this disease process alone), would have very low amounts of DNA present in the cyst fluid, because the lining cells of the cyst contain very few cells, which replicate very slowly. It is further believed that low grade, slow growing, neoplastic processes (such as, but not limited to, a benign mucinous cystadenoma), would generate an associated cyst fluid that contained relatively greater amounts of DNA that would be relatively more intact given the greater turnover of replicating lining cells. Finally, it is further believed that a malignant tumor (such as, but not limited to, an early pancreatic adenocarcinoma), would possess the highest amounts of DNA of highest quality and intactness in associated cystic fluid. To confirm this belief, a novel approach as set forth herein was created to quantitatively define the amount and integrity of cyst fluid DNA, and then demonstrate statistically significant thresholds that would separate non-neoplastic, indolent, and malignant pancreatic states from each other. The combined applications of these concepts to pathology analysis of pancreatic cyst fluid and the specific methods used were uniquely created to address these needs.

The approach includes the direct quantitation of extracted DNA using established optical density measurement technique, and the qPCR determination of DNA concentration. Herein, the qPCR reaction is used not used to measure DNA concentration as that is accomplished by the first step optical density measurement. Rather the optical density concentration is used to standardize the qPCR reaction to a starting concentration of 5 ng/μL. The variation in the qPCR reaction then serves as a measure of the degree of intactness of DNA since the highest qPCR values for DNA starting concentration will be seen when DNA has not undergone degradation. This use of the qPCR to inform not on DNA starting concentration but on DNA integrity is novel.

1. Acronyms and Definitions 1.1 Acronyms

In accordance with this detailed description, the following abbreviations and definitions apply. It must be noted that as used herein, the singular forms "a," "and," and "the" include plural referents unless the context clearly dictates otherwise. Thus, for example, reference to "an antibody" includes a plurality of such antibodies and reference to "the dosage" includes reference to one or more dosages and equivalents thereof known to those skilled in the art, and so forth.

APC activated protein C
CEA carcinogenic antigen
EUS endoscopic ultrasound
FNA fine needle aspiration
HGD high grade dysplasia
IPMN intraductal pancreatic mucinous neoplasm
LOH loss of heterozygosity
MCA mucinous cystadenoma
MCN mucinous cystic neoplasms
OD optical density
PanIN pancreatic intraductal neoplasia
PCR polymerase chain amplification reaction
qPCR quantitative polymerase chain reaction
ROC receiver operating characteristic
SO standard deviation
VHL Von Hippel-Lindau disease 1.2 Definitions By "pancreatic anomaly" is meant a broad, encompassing term to indicate a disease related change in the pancreas. By "pre-cancerous pancreatic state" is meant defined structural alterations that precede the later development of pancreatic cancer. Currently our understanding of pancreatic cursor lesions is quite limited however current efforts to clarify these alterations will do much to enhance understanding of those cellular changes leading to pancreatic cancer formation.

By "non-neoplastic condition" is meant a broad, encompassing term to indicate cancer not arising from the pancreatic ductal lining epithelial cells.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

2. Pancreatic Conditions

Incidence of carcinoma of the pancreas has markedly increased over the past several decades, and ranks as the fourth leading cause of cancer death in the United States. Cancer of the exocrine pancreas is rarely curable and has an overall survival rate of less than 4%. For patients with advanced pancreatic cancers, the overall survival rate of all stages is less than 1% at 5 years with most patients dying within 1 year.

There are many types of pancreatic cancer, including but not limited to malignant duct cell carcinoma; acinar cell carcinoma; papillary mucinous carcinoma; signet ring carcinoma; adenosquamous carcinoma; undifferentiated carcinoma; mucinous carcinoma; giant cell carcinoma; small cell carcinoma; cystadenocarcinoma; unclassified, pancreatoblastoma; papillary-cystic neoplasm; mucinous cystic tumor with dysplasia; intraductal papillary mucinous tumor with dysplasia; and pseudopapillary solid tumor.

Papillary-cystic neoplasm of the pancreas is a rare neoplasm principally affecting young women. It has a favourable prognosis and has a low grade malignant potential, and is known by different names such as Frantz's Tumor, solid and cystic tumor and solid and epithelial neoplasm.

Acute pancreatitis is an acute inflammatory process of the pancreas that can also involve peripancreatic tissues and/or remote organ systems. Severe pancreatitis is characterized by the presence of organ failure (including shock, pulmonary insufficiency, renal failure and gastrointestinal bleeding) and/or the presence of local complications, such as pancreatic necrosis, abscess or pseudocyst. When the pancreatic fluid extravasates out of the pancreas, it collects in the anterior pararenal space and other areas. If it persists for more than four weeks, it becomes encapsulated in a wall and develops into a pseudocyst. Severe pancreatitis may also be complicated by pseudocyst or pancreatic abscess formation. Pseudocysts occur in approximately 20% of cases and should be drained only if causing symptoms.

Pancreatic cancer has a poor prognosis, with a 5-year survival rate of less than 5%. For patients with unresectable pancreatic cancers, median survival is only 19 weeks with the best of the combination chemotherapy regimens. For patients treated with both chemotherapy and radiation, median survival increase to only about 11 months.

Mutations such those involving codon 12 of K-ras oncogene, c-erb B-12 oncogene, and p-16 tumor suppressor gene have been described. Tumor markers such as Ca19-9, islet amyloid polypeptide, and CEA are elevated in patients with pancreatic cancer but lack sufficient sensitivity or specificity.

Cystic neoplasms account for less than 1% of pancreatic tumors. These include serous cystadenomas, mucinous cystic neoplasms, intraductal papillary mucinous tumor, and papillary cystic epithelial neoplasia. Serous cystadenomas are benign cystic tumors lined by cuboidal epithelium with a central stellate calcification. Mucinous cystic neoplasms (MCN) are lined with columnar epithelium and have a varying malignancy potential ranging from benign adenomas to malignant cystadenocarcinomas.

Pancreatic MCN are unique in that they are discovered at varying points along the benign to malignant spectrum. The overwhelming concern when faced with this diagnosis is the presence of occult or impending cancer. A recent report indicated that the cyst aspirate CEA level is currently the most accurate predictor of MCN.

Discoveries from the Human Genome Project raise the possibility of improved diagnostic approaches, which may be applied to these small but representative samples from pancreatic cysts. The altered morphology of malignant cells reflects underlying genetic changes. The progressive morphologic changes seen in the development of pancreatic ductal adenocarcinoma from normal cells has been modeled in the now familiar pancreatic intraductal neoplasia (PanIN) system (Apple, et. al., *Hum. Pathol.* 1999, 30: 123-9). This system includes standardized pathologic criteria for each progressive stage in tumor development linked with the underlying genetic aberrations (Mizumoto, et al. *J. Hepatobiliary Pancreat. Surg.* 2002, 9: 39-44). For example, K-ras codon 12 mutations represent one of the earliest genetic changes in the development of pancreatic ductal cancer (Wilentz, et. al. *Cancer Res.* 2000, 60: 2002-6). Sequential inactivation of tumor suppressor genes is also seen. This process can occur through a variety of processes including gene mutation, hypermethylation, or loss of a chromosome or chromosomal segment containing the tumor suppressor gene. Any combination of these events will lead to loss of tumor suppressor gene activity.

The explanation lies in the biology of pancreatic MCN. Neoplastic change is a continuous process first occurring at the sub-cellular stage, followed by cellular morphologic change. Lesion pathology is a subjective evaluation at one point in time, whereas detailed DNA analysis provides information into a lesion's future, as well as its current state.

Other aspects of pancreatic carcinogenesis that lack clarity are the pattern and rate of mutation accumulation. The unique weight or significance of each individual mutation and whether this "weight" varies with the timing of occurrence in relation to other mutations is unknown.

A detailed molecular analysis incorporating DNA quality and quantity, K-ras mutational analysis, and a broad spectrum of tumor suppressor gene linked microsatellite LOH can be used to predict the presence of invasive cancer or high grade dysplasia, pre-cancerous conditions or other pancreatic states.

Von Hippel-Lindau Disease (VHL) is an inherited multisystem disorder characterized by the abnormal growth of blood vessels in certain parts of the body (angiomatosis). Capillaries join to form angiomas, which may develop in areas of the body such as the retina, brain, spinal cord and the adrenal glands. The symptoms of VHL vary greatly and depend on the size and location of the growths. Patients with VHL are genetically predisposed to certain types of malignant tumors such as renal cell carcinoma. DEVITA, JR. ET AL. CANCER: PRINCIPLES & PRACTICE ON ONCOLOGY, 1255-1272 (5$^{th}$ Ed., New York: Lippincot-Raven Publishers, 1997).

In light of the prevalence and severity of the above conditions, as well as other conditions affecting the pancreas, there is a need for an effective method of predicting, diagnosis and treating these pancreatic conditions.

3. Procedures

The methods described herein are useful in the prediction, treatment and diagnosis of pancreatic anomalies. The methods comprise obtaining a pancreatic aspirate, extracting DNA from the aspirate, quantifying the DNA, analyzing the quality of the DNA, and performing mutational and other molecular analysis on the DNA.

3.1 Obtaining Aspirate

Pancreatic cyst aspiration may be obtained through methods known in the art. The two most commonly used methods are to utilize imaging via endoscopic ultrasound or by abdominal CT or MRI. However, any technique to collect pancreatic fluid DNA with or without associated imaging will serve adequately. A wide collection of standard textbooks are available.

Preferably, the histopathology and cytopathology associated with the cyst fluid should first be reviewed, as well as the clinical information pertinent to the individual patient. However, fluid genotyping can be performed without preliminary review of microscopic features. The fluid sample can be examined by naked eye to note its color, clarity and character. For example, if the fluid contains abundant blood this should be taken into account due to effects directly related to the blood. The presence of the blood could affect the results, and thus should be accounted for when reviewing the final results of the methods of the present invention. Thus, the analysis of the results and the methods of the present invention are preferably performed by a one of skill in the art familiar with medicine and pathology practice. These preliminary observations are suggestion and do not necessarily need to be performed as a prelude to topographic genotyping of pancreatic fluid.

3.2 Extraction of DNA from the Pancreatic Cyst Fluid

The molecular analysis begins by extracting DNA from the pancreatic cyst fluid. This is accomplished by first treating the sample with proteinase (Proteinase K), and then capturing the DNA on a spin column while eluting the protein, salts and other unwanted constituents. Preferably, DNA is extracted from a pancreatic fluid by column separation, though any methods known to the skilled artisan are acceptable. This can be readily accomplished using, for example, the Qiagen spin column, though all other techniques to selectively isolate DNA would serve just as well. Any technique that extracts DNA from a biological fluid or tissue samples could substitute quite adequately. If sufficient DNA is present in the fluid sample, it may be used directly bypassing the step of DNA extraction. The extracted DNA need not be highly purified or clean but may be used directly following simple extraction. Highly purified DNA or other DNA preparation can substitute though this is not required.

3.3 Quantitation of DNA for DNA Quantity and Quality Analysis

Optical density (OD) analysis is then performed to quantify the DNA. One approach uses the Nanodrop technique, because it requires only one microliter to be sacrificed for the purpose of obtaining the DNA concentration (Ding and Cantor, 2004 *J. Biochem. & Mol. Biol.* 37(1):1-10). Other techniques for quantifying DNA will serve quite adequately for this purpose.

A higher optical density (OD) value indicates a larger amount of DNA. The quantity of DNA extracted can vary. However, the higher the amount of DNA, the more likely high grade dysplasia or malignancy is present. In testing of over 200 patients, it has been shown that samples with an OD value of about 2.0 ng/µL or less are considered to have insufficient DNA. Values in the range of about 2.0-7.5 (and any 0.1 OD value in between) indicate pre-cancerous pancreatic lesions or low grade indolent forms of pancreatic neoplasia. Values over about 7.5 are highly indicative of the presence of malignancy, e.g., values of about 8.0 to about 650 or any integer value in between, although values may be higher. These conclusions are not definitive, but only suggestive and are to be used with the other data obtained by the methods described herein to come to a definitive assessment.

The DNA can be quantified by measurement of the optical density to fluorescent light at wavelengths of 230, 260, and 280 nm. The 260/280 and 260/230 ratios should be 1.7-2.0, in keeping with extraction of purified DNA and for the purpose to exclude protein and other contaminants. Any technique that defines the amount of DNA in the sample can be a suitable substitute.

3.4 Determination of DNA Quality for DNA Quantity and Quality Analysis

To measure DNA quality, quantitative PCR (qPCR) is performed first followed by competitive template PCR. Using the concept that a longer sized PCR product would be present in relatively lesser amounts than a shorter sized product due to greater chance for strand breakage as a result of DNA degradation, a competitive duplex PCR reaction of highly similar DNA sequence but differing in length was needed. This can easily be accomplished by simply carrying out a short and long product PCR reaction in one container (e.g., test tube) on one source of DNA. Unfortunately, the duplex reactions are not equivalent, because they use different primers and generate radically different products. Moreover, the status of the PCR reaction must be carefully controlled since amplification is not the same during the different phases of the reaction (i.e., exponential phase versus plateau phase). The methods described herein overcome this obstacle.

The human genome was searched for gene/pseudogene pairings that possessed the identical genomic sequence except for a segment present in one that was deleted in the other. The only difference in precise genomic sequence was the deleted segment which could vary in length. The greater the deletional length difference, the greater would be the ability to detect differences related to DNA degradation. Most importantly, the primer hybridization sites for PCR would be identical and the relative amounts of product made would be essentially independent of the status of the PCR reaction itself. Two such gene/pseudogene pairings were found though the approach would be applicable to any other pairing of genomic segments differing only by a deletional region or regions. These genes are the glucocerebrosidase gene (GenBank D13286) and its pseudogene (GenBank D13287) and the CEL gene (Genbank M94579) and its pseudogene (GenBank M94580). Other similar examples may also be employed.

The competitive template PCR reaction for the glucocerebrosidase gene/pseudogene pairing (exon 9) provided a novel highly sensitive means to quantitate the degree of DNA degradation. The results from this assay, together with that from optical density measurement and qPCR, provided highly discriminating information on DNA degradation. This information in turn proved highly useful in separating the conditions listed in Table 1. With the current techniques used in the art, these conditions are only poorly discriminated in fine needle biopsy cytology specimens using microscopic evaluation.

TABLE 1

Pancreatic Anomalies

| PANCREATIC CANCER | PRE-CANCER STATES | NON-NEOPLASTIC STATES |
|---|---|---|
| Pancreatic ductal adenocarcinoma | Mucinous cystadenoma | Pancreatitis |
| Pancreatic Acinar Cell Carcinoma | Serous cystadenoma | Pancreatic pseudocyst |
| Neuroendocrine Cell Carcinoma | Islet cell tumor | Mesothelial cyst |
| Sarcoma of the Pancreas | Mucinous Duct Ectasia | Lymphoepithelial cyst of the pancreas |
| Metastatic cancer involving the pancreas | Intraductal Papillary Mucinous Neoplasm | Ischemic necrosis of the pancreas |
| Pancreaticoblastoma | Pancreatic Intraepithelial Neoplasia (PanIN grades 1-3) | |
| Bile Duct Carcinoma (Cholangiocarcinoma) | Solid and Cystic Papillary Tumor of the Pancreas | |

Genetic research on pancreatic cancer, including those molecular changes that may be important during the earlier phases of development and progression, has documented a wide range of tumor suppressor genes, oncogenes and other molecular changes. These are summarized in Table 2 which does not attempt to include all known aberrations. Other gene mutations are likely to be discovered in the near future.

TABLE 2

Genetic Mutations in Pancreatic Cancer

| TUMOR SUPPRESSOR GENES | ONCOGENES | OTHER MUTATIONS AND ALTERATIONS |
|---|---|---|
| TP53 | K-RAS-2 | MICROSATELLITE INSTABILITY |
| P16 | EPIDERMAL GROWTH FACTOR RECEPTOR | GENE REARRANGEMENTS |
| PTEN | | |
| RETINOBLASTOMA | | |

As described above, detection of cumulative mutations represents an important aspect of the molecular pathology approach for early detection of pancreatic cancer. It is recognized however that the total detectable mutation complement in an individual patient may in fact be relatively few in total amount in keeping with the early stage of cancer development. At the same time, related conditions such as pancreatic pre-cancer states and non-neoplastic states will themselves possess few or no detectable mutations. Hence, the need to incorporate DNA quantity and quality analysis is addressed by the embodiments disclosed herein. Another aspect of the invention relates to the essential need to make greater use of the few detectable mutations that will be determined. This in turn involves delineating the time course of detectable mutation accumulation in addition to simply noting the presence or absence of one or more mutations.

A novel approach was created to determine the time course of mutation accumulation (FIGS. 1A and B). The approach is based on the well established concept of clonal expansion of phenotypically more aggressive tumor cells. Clonal expansion is a unidirectional process replacing precursor neoplastic cells with a dominant tumor cell population of cells with progressively more mutations (FIGS. 1A and B).

The first approach is carried out in tissue section using a microdissection genotyping technique (FIG. 1A). Mutations present over a wider area of tumor were acquired earlier in tumor development. Mutations present focally are acquired relatively more recently. This first method for time course delineation is used to evaluate the resected pancreatic tissue as an important quality control measure to assess time course delineation in fluid samples.

Figure 1B:
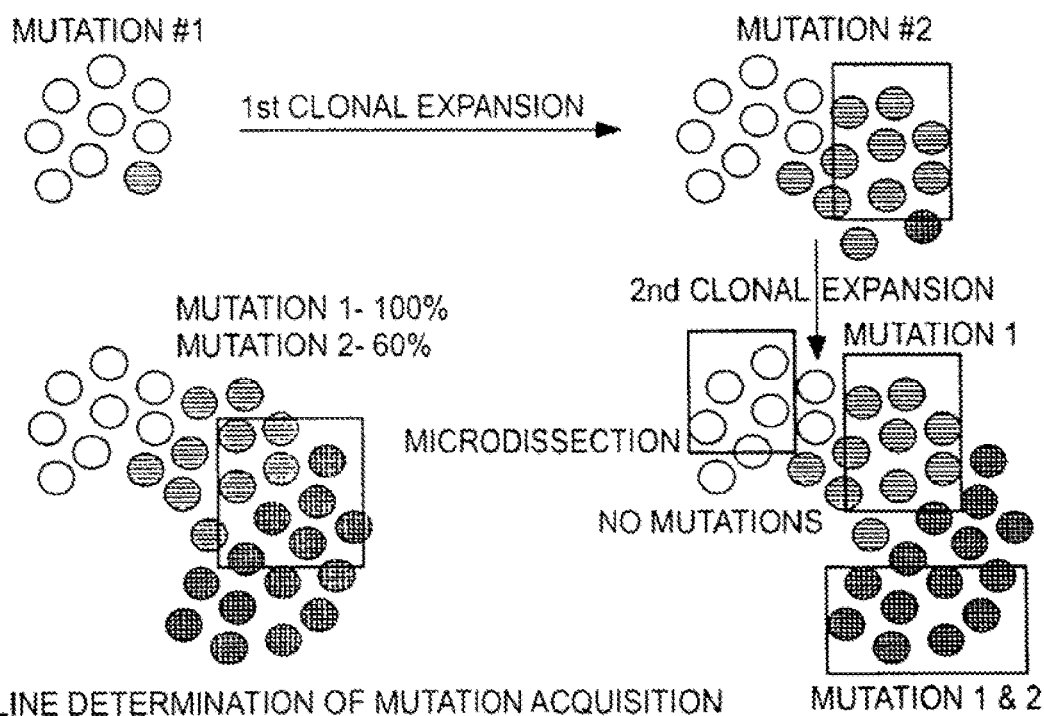

The second approach is shown in FIG. 1B. Quantitative determination of allelic imbalance mutation or other forms of mutation are arranged according to the degree of relative DNA involvement. Mutations with greater DNA involvement can be assigned earlier temporal acquisition while those with relatively lesser involvement can be defined as occurring later in time.

Thus, the invention encompasses a series of quantitative maneuvers to define both the DNA, as a whole, and specific accumulated mutations. The DNA is assessed for quantity and integrity, the latter using novel assays designed to measure DNA degradation. Cumulative mutations are measured not just for their presence but for their time course of acquisition. These provide the necessary end points upon which to critically evaluate pancreatic fluids for early detection of pancreatic cancer while at the same time objectively discriminating similar appearing non-neoplastic and indolent neoplastic anomalies that may be confused with the early cancer detection process. This innovative approach provides a new means to characterize cancer and pre-cancer states in a manner that will greatly improve their diagnosis and treatment.

To measure DNA quality, quantitative PCR (qPCR) is performed and is followed by competitive template PCR. The qPCR reaction can be performed using sybr green as the indicator in a suitable thermocycler capable of measuring fluorescence during the amplification process as this is the simplest and least costly technique. Other techniques for qPCR determination using fluorescent labeled primers can substitute just as well. Known quantitative controls and replicate analysis of samples may be used to standardize amplification reactions and is recommended; the exact use and configuration of controls and replicate analysis may be varied as determined by the user. Standardization of quantitative PCR amplification of the first exon of the K-ras-2 gene may be used for this purpose in this invention. However, any PCR product from any gene or genomic segment may be effectively used.

The first step in the qPCR process is to adjust the extracted sample DNA concentration to a value of about 5 ng/µg so that the absolute amount of DNA present in each reaction is the same, but so that the integrity may vary which is the purpose of the analysis. 5 ng/µL is preferred as it has been found to be a minimal value for robust amplification. However, other amounts may be used. For example, from about 10 ng to about 10 µg and more preferably from about 5 ng to about 5 µg may be used. All other values may be substituted quite freely and is up to the discretion of the investigator.

The number of qPCR cycles may be used as a marker of DNA quality. The lower the number cycles required to reach a desired threshold is indicative of higher quality DNA. In general, if over 30 cycles are required, then the DNA quality is considered suboptimal due to, for example, allelic imbalance resulting from inadequate amounts of template DNA. Specifically, Ct values (i.e., threshold values for quantitative PCR product detection) over 30.0 cycles is considered evidence of poor quality of DNA, especially if the DNA quantity present is above 2.0 ng/µL. Ct values of 29.0-30.0 are considered borderline. Values of 29.0 or less are indicative of good quality DNA. Additionally, values of 29.0 or less may indicate the presence of neoplasia. The lower the Ct value, the more likely neoplastic cell proliferation is malignant. These values may vary based on the conditions and amounts employed. For example, cancers that are slow growing, well-differentiated in growth pattern and relatively less cellular may be expected to show borderline Ct values that are significantly higher than 29-30 cycles.

3.5 Competitive Template Nucleic Acid Amplification to Assess DNA Quality

DNA quality may be further assessed by performing competitive template PCR amplification for a unique pair of genes, (e.g., Glucocerebrosidase Gene and its Pseudogene) at a particular point where the two genes have virtually identical sequences, with the exception of a 55 base pair deletion in the pseudogene. This is not the only gene that can serve this purpose. In fact any pairing of gene or genomic segments of similar sequence but differences in length can be substituted.

This PCR reaction creates two amplicons that are identical in sequence except for the deletional region. During the reaction, a competition exists between the two similar templates (but having different lengths). The degree of DNA degradation in the sample will be reflected by less effective amplification of the longer template as compared to the shorter template. This serves as a measure of DNA integrity. The amount of each product, short and long, may be quantitatively measured by capillary electrophoresis. Methods of performing the PCR reaction and electrophoresis are well known in the art. A non-neoplastic process shows prominent DNA degradation, while a malignancy is associated with the presence of abundant, good quality DNA. Reagents are added to the final sample the purpose of which is to enhance DNA availability, to enhance the ability to amplify the DNA, and DNA quantity.

While the use of two highly similar amplification targets is recommended, any system that utilizes similar primers to amplify products of different lengths can be substituted. The genetic targets used should be such as to produce different sized products under similar amplification conditions in the target tissue specimens and thus is essentially independent of specimen fixation or preparation effects. The closer to the value one 1.00 the ratio of amplified product to each product is, the better the quality of DNA.

The procedure for PCR amplification has been well described and variations on its performance will not impact the invention. As described in the Examples below, the recommended procedures of the manufacturers for the PCR reagents is closely followed (GeneAmp kit, Applied Biosystems). However, other commercial and non-commercial systems for PCR amplification can be readily substituted. It is preferred that the PCR reaction is performed in a manner that is highly robust, especially when using minute samples such as dilute fluid specimens. By "robust" in this context is meant a PCR reaction that reliably generates abundant amplified DNA that accurately reflect the starting composition mixture of normal and mutated DNA derived from a particular specimen. Reagents such as dimethylsufoxide or dextran sulfate may be added to the amplification reaction to enhance amplification. Other similar reagents can be substituted. Also, manipulations, such as nested PCR, may be performed to further enhance amplification. Other similar steps may be used though they are not mandatory.

3.6 Mutation Analysis and Other Molecular Analysis of DNA in Aspirate

Parallel progression of cellular neoplasia and DNA mutational damage in pancreatic cancer has been described (see, e.g. Mizumoto, et al. *J. Hepatobiliary Pancreat. Surg.* 2002 9: 39-44). However such work examined the mutational damage only in the context of traditional pathology microscopic review. The invention described herein provides examination of the cell aspirate. Pancreatic cyst aspirates are usually not available for accurate diagnosis. Another option is to look for mutations in the free-floating DNA that exists in the pancreatic cyst aspirates by using surrogate markers of cellular neoplastic transformation. The free floating DNA would have originated from the nuclear DNA of cells lining the cyst or in direct contact with the cyst fluid. It is these cells that produced the cyst and provide the basis for diagnosis and characterization of the pancreatic cyst and associated condition.

At this point it is useful to distinguish clearly between the different types of DNA that will apply to this situation of laboratory evaluation. The DNA of critical interest is the DNA of the cells that are responsible for the pancreatic anomaly. It is this DNA that represents the anomaly of interest including early pancreatic cancer. The cyst fluid will contain the DNA released from these critical cells of interest. However, the amount and intactness will depend upon the active turnover of cells as described above. The DNA in the cyst fluid can be referred to as free floating DNA. Due to the physicochemical properties of DNA, part or all may not remain free floating but may become attached to either the sides of the tubing used to collect the fluid and maintain it, or it may attach nonspecifically to the surface of any cells present in the cyst fluid. Thus, when the analysis is performed on the cyst fluid, the DNA being evaluated may be a combination of nuclear DNA in detached cells present in the cyst fluid as well as free floating DNA from critical lining cells and secondarily attached to detached cells. The DNA will be in greater amounts and have better integrity (quality) if the underlying cause of the cyst is more malignant.

Representative cells lining malignant cysts are theorized to manifest a high level of accumulated mutational damage reflective of an underlying malignancy. High levels of accumulated mutational damage would not be seen in cells in a benign cyst. An inflammatory process in the pancreas would not be expected to manifest evidence of cumulative mutational change. A higher degree of cell turnover may also occur in the lining of a malignant cyst, thus releasing high amounts and quality of mutated DNA into the cyst fluid.

Because chromosomal allelic loss, commonly referred to as loss of heterozygosity (LOH), is a major cause of tumor suppressor gene inactivation, detection of LOH from microsatellite markers closely linked to key tumor suppressor genes serves as an excellent surrogate marker for gene inactivation. The present invention uses a panel of LOH markers along with K-ras codon 12 oncogene activation mutation detection on EUS aspirates from pancreatic cysts, together with analysis of DNA quality and quantity to predict the presence of pancreatic cancer or neoplasia, and to diagnose and treat these conditions.

While mutation detection is regarded as a means to characterize cancer, assessment of the quality and quantity of DNA has never been employed to achieve this objective.

This assessment of DNA is not intuitive. In pathology, the emphasis had always been on detection of mutations, which is suitable for detecting advanced forms of cancer that bear abundant mutational damage. Many studies have documented the striking difference with respect to the presence or absence of mutations when comparing advanced cancer to a non-cancerous process of the same tissue type. This however would not be of value in the early detection of cancer where accumulated mutations would be relatively few. An alternative end point is required to objectively separate early cancer from indolent forms of neoplasia (benign tumors) and from similar appearing non-neoplastic states.

One aspect of the present invention provides a method for predicting the presence of a pancreatic anomaly in a patient suffering from pancreatic cysts comprising
  a) performing molecular analysis of DNA from an aspirate from a patient pancreatic cyst comprising
    (i) performing an optical density analysis of the aspirate to determine DNA quantity;
    (ii) performing a quantitative PCR analysis of the aspirate to determine DNA quality;
    (iii) performing competitive template PCR to further quantify DNA quality; and
  b) performing mutation analysis of the DNA in the aspirate comprising:
    (i) determining the presence of mutations in a tumor suppressor gene and/or the presence of a cancer related genetic marker,
    (ii) determining tumor suppressor gene loss of heterozygosity (LOH) by catalyzing polymorphic microsatellites or other polymorphic markers linked to tumor suppressor genes;
    (iii) determining point mutations in the K-ras oncogene and/or point mutations in at least one other cancer-associated gene;
    (iv) determining other structural alterations in DNA;
    (v) determining the percentage of mutated DNA from steps b)(ii) and b)(iii); and
    (vi) determining the specific temporal sequence of mutation accumulation based on step (v) wherein the temporal sequence of mutation accumulation is predictive of the presence of a pancreatic anomaly.

The method may further comprise confirming the results of steps a) and/or b) by comparison with pathologic analysis of a cystic lesion surgically obtained from the patient. The method can further comprise analyzing the cyst carcinoembryonic antigen (CEA) level (or other specified biomarker) of the aspirate by any means known in the art.

The DNA in the aspirate may be free-floating or free and adherent to the surface of cells or tissue constituents of the cyst. DNA possesses a physicochemical tendency to adhere to biological surfaces such as cell membranes as well as physical structures such as glass or plastic. From these locations the DNA can be extracted and analyzed. This DNA is derived from cells that line or are in contact with a fluid collection and thus is representative of those cellular elements that constitute the cyst. The free or surface attached DNA is not visible by microscopic examination. However, it can be extracted and analyzed as a means to assess the etiology and character of a pancreatic cystic alteration. The same concepts hold true for pancreatic fluid moving through a channel, such as the pancreatic ductal system. It will contain both intact cells with internal nuclear DNA, as well as free genomic DNA both sources of which provide DNA that can be used to determine the characteristics of the lining cells. In addition to searching for mutations, the quantity and amplifiable quality of the DNA can serve as end points for the analysis of DNA. Preferably, the cycles of quantitative PCR performed in step a) (ii) is greater than a threshold unique for that specific type of DNA. Preferably, the cycles of quantitative PCR performed in step a) (ii) is less than or equal to 29, although it may also be 29-30 or thirty or more.

Preferably, the optical density is about 2.0 to about 7.5. Also preferably, the optical density is greater than 7.5. Preferably, the allele ratio is two standard deviations beyond the average for the ratio of the specific pairing of polymorphic alleles.

Preferably, the patient is a mammal. More, preferably, the patient is a human.

Preferably, the pancreatic anomaly is a pancreatic cancer or dysplasia, pre-cancerous pancreatic state or non-neoplastic condition or non-neoplastic condition that presents with similar clinical or pathologic features so as to be potentially confused with pancreatic cancer. The pancreatic cancer or dysplasia may include, but is not limited to, pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma). The pre-cancerous pancreatic state may include, but is not limited to mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may include, but is not limited to, pancreatitis, pancreatic pseudocyst, mesothelial cyst, lymphoepithelial cyst of the pancreas, and ischemic necrosis of the pancreas.

Another aspect of the present invention includes a method for diagnosing a pancreatic anomaly in a patient suffering from pancreatic cysts comprising
  a) performing molecular analysis of DNA from an aspirate from a patient pancreatic cyst comprising:
    (i) performing an optical density analysis of the aspirate to determine DNA quantity;
    (ii) performing a quantitative PCR analysis of the aspirate to determine DNA quality;
    (iii) performing competitive template PCR to determine DNA quality; and
  b) performing mutation analysis of the DNA in the aspirate comprising:
    (i) determining the presence of mutations in a tumor suppressor gene and/or the presence of a cancer related genetic marker;
    (ii) determining tumor suppressor gene loss of heterozygosity (LOH) by catalyzing polymorphic microsatellites or other polymorphic markers linked to tumor suppressor genes;
    (iii) determining point mutations in the K-ras oncogene and/or point mutations in at least one other cancer-associated gene;
    (iv) determining other structural alterations in DNA;
    (v) determining the percentage of mutated DNA from steps b)(ii) and b)(iii); and
    (vi) determining the specific temporal sequence of mutation accumulation based on step (v), wherein the results of steps a) and b) are used to diagnose a pancreatic anomaly in a patient.

Preferably, the pancreatic anomaly is a pancreatic cancer or dysplasia, pre-cancerous pancreatic state or non-neoplastic condition. The pancreatic cancer or dysplasia may include, but is not limited to, pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma). The pro-cancerous pancreatic state may include, but is not limited to mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may include, but is not limited to, pancreatitis, pancreatic pseudocyst, mesothelial cyst, lymphoepithelial cyst of the pancreas, and ischemic necrosis of the pancreas.

A further aspect of the invention includes a method for determining a course of treatment for a pancreatic anomaly in a patient suffering from pancreatic cysts comprising:
a) performing molecular analysis of DNA from an aspirate from a patient pancreatic cyst comprising
  (i) performing an optical density analysis of the aspirate to determine DNA quantity;
  (ii) performing a quantitative PCR analysis of the aspirate to determine DNA quality;
  (iii) performing competitive template PCR to determine DNA quality; and
b) performing mutation analysis of the DNA in the aspirate comprising
  (i) determining the presence of mutations in a tumor suppressor gene and/or the presence of a cancer related genetic marker;
  (ii) determining tumor suppressor gene loss of heterozygosity (LOH) by catalyzing polymorphic microsatellites or other polymorphic markers linked to tumor suppressor genes;
  (iii) determining point mutations in the K-ras oncogene and/or point mutations in at least one other cancer-associated gene;
  (iv) determining other structural alterations in DNA;
  (v) determining the percentage of mutated DNA from steps b)(ii) and b)(iii); and
  (vi) determining the specific temporal sequence of mutation accumulation based on step (v), wherein the results of steps a) and b) are used to determine a course of therapy for a patient suffering from a pancreatic anomaly.

Preferably, the pancreatic anomaly is a pancreatic cancer or dysplasia, pre-cancerous pancreatic state or non-neoplastic condition. The pancreatic cancer or dysplasia may include, but is not limited to, pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma). The pre-cancerous pancreatic state may include, but is not limited to mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas. The non-neoplastic condition may include, but is not limited to, pancreatitis, pancreatic pseudocyst, mesothelial cyst, lymphoepithelial cyst of the pancreas, and ischemic necrosis of the pancreas.

A further aspect of the present invention includes a method of determining whether a pancreatic cyst is malignant comprising performing a qualitative DNA analysis on aspirate from the cyst, wherein the qualitative DNA analysis comprises performing PCR amplification for a glucocerosidase gene and its pseudogene at a point where the two genes have identical sequences except for a 55 base pair deletion in the pseudogene; and measuring the amount of product from PCR amplification by capillary electrophoresis.

A tumor suppressor gene panel and panel of other cancer related genes are assembled to be applied to the aspirate. The pancreatic cyst aspirate is also subjected to DNA mutational analysis. Pancreatic cyst aspirate may be amplified using PCR for a broad panel of tumor suppressor genes or other genes commonly involved in human pancreatic carcinogenesis. Tumor suppressor gene loss of heterozygosity (LOH) was determined by analysis of tightly linked, informative polymorphic microsatellites.

A microsatellite is a string of 1 to 4 nucleotides that are repeated over a short distance within a region of genomic DNA. The number of repeats and the locus is often variable between alleles, such that each chromosome is identifiable and can be traced. Because a multitude of microsatellites with variable lengths span the human genome, it is possible to choose highly heterogeneous microsatellites as chromosomal markers at loci in close proximity to a tumor suppressor gene. Loss of heterozygosity (LOH), e.g. either the shorter or longer microsatellite is missing, suggests that one of the two chromosomal arms has been lost. Thus, a mutation of the tumor suppressor gene on the opposite chromosomal arm conferes a growth advantage to the clone of tumor cells with this combination of LOH.

Use of two markers within each locus was used to increase the likelihood that at least one of the markers would be polymorphic within a subject, and thus informative for LOH analysis.

PCR amplification may be used to generate amplicons of less than 200 nucleotides using synthetic oligonucleotide primers flanking each microsatellite. Allele peak heights and lengths may be used to define the presence or absence of allelic imbalance (i.e., LOH) for a given sample. Allelic imbalance is reported when the ratio of polymorphic allelic bands for a particular marker is beyond about 95% confidence limits for the variation in peak heights for individual allele pairings derived from analysis using non-neoplastic specimen samples. In general, this value was below 0.5 or above 2.0. Preferably, the allele ratio is two standard deviations beyond the average for the ratio of the specific pairing of polymorphic alleles. This will provide the lowest threshold for detection of significant allelic imbalance (LOH) however other algorthims for defining LOH can be used, so long as they are applied uniformly across different specimens. It is understood that minor degrees of LOH will not be detected. However, this is not a drawback, because these minor LOH mutations may not be causally related to clonal expansion or provides significant malignant growth properties.

Allelic imbalance mutations are treated as genomic deletions associated with tumor suppressor genes. The ratio of allele peak heights is a measure of an admixture of mutated and non-mutated cells or DNA, and varies according to the individual pairing of specific microsatellite marker alleles. Allele ratios of 2.0 or 0.5 is said to be present when 50% of the total DNA is derived from cells possessing the loss. The deviation from ideal normal ratio of 1.0 indicates which specific allele was affected. Allele ratios below about 0.5 or above about 2.0 are mathematically correlated with the proportion of cells affected by genomic loss. The order of mutation acquisition may be arranged in a temporal sequence of mutation acquisition reflecting the proportion of cells affected by specific microsatellite marker loss (FIG. 2). Markers displaying more extreme ratios are considered to have been acquired earlier in the disease process. This conclusion is based on the premise of clonal expansion; a cloned expansion occurs when tumor cell populations progressively replace each other by accruing mutations which are causally associated with increasing malignant phenotype.

3.7 Determination of Chronology of Mutation Acquisition

Determination of the temporal sequence of mutation acquisition had never before been effectively performed on fixative treated clinical specimen or in a clinical context. Delineation of the time course of mutation acquisition is provided herein and is important to the diagnosis prognosis and treatment of the patient's disease. The identical profile of mutations between different individual patients with the same microscopic form of cancer may not be expected to behave in exactly the same manner. The order by which the mutations are accumulated may greatly influence the final biological behavior. This is especially true for response to treatment where earlier acquisition of treatment responsive mutations will be associated with greater therapeutic effect in the treated subject due to the presence of those mutations (see FIG. 2). For example, it is shown that gliomas which acquire the 1p/19q deletion earlier in tumorigenesis are more responsive to treatment than gliomas that do not have this deletion early in tumorigenesis.

Assuming a model of allelic loss with minimal non-neoplastic cell DNA inclusion, the percentage of mutated DNA may be determined for each marker. When two or more mutations, (e.g., K-ras-2 and/or allelic imbalance mutations), are detected, their time course of accumulation is inferred by the proportion of total DNA manifesting the alteration. In the case of K-ras-2 oncogene point mutation, involvement of 100% of cells is considered to be present when the intensity of the mutated base on sequencing is equal to or greater than the normal sequence base pair. This may be determined qualitatively by visual comparison or more precisely by quantitation. Any method that provides relative amounts of mutated cell population could substitute effectively.

During the final evaluation of all the data from the methods of the present invention, the presence of mutational change must first be analyzed with respect to the quantity and quality of DNA. It is important to do this analysis of mutational change, because the presence of low amounts of poor quality DNA can produce false positive detection of deletion type mutations due to a phenomenon in the PCR reaction called allelic drop-out.

These analytical methods may be used to diagnose pancreatic cancer, pre-cancerous pancreatic states or non-neoplastic conditions. The analytical methods may also be used to determine the prognosis for a patient suffering from pancreatic cancer, pre-cancerous pancreatic state, or non-neoplastic condition. The analytical methods may be further used to determine a course of therapy for a patient suffering from pancreatic cancer, pre-cancerous pancreatic state, or alternative pancreatic neoplastic condition, as discussed herein. Because the methods of the present invention allow for sensitive prediction of cancer and pre-cancerous conditions, a physician or other of skill in the art can use the methods to more accurately determine the prognosis of the pancreatic condition. Furthermore, if a physician has advanced warning that cancer is present, treatment may be begun earlier and more carefully tailored to the condition (including surgery, radiation therapy, chemotherapy, and biologic therapy). To this end, the physician skilled in the art will be familiar with diagnosis, prognosis and treatment of pancreatic anomalies. See, for example, DEVITA, JR. ET AL. CANCER: PRINCIPLES & PRACTICE ON ONCOLOGY, volumes 1 and 2 ($5^{th}$ Ed., New York: Lippincott-Raven Publishers, 1997).

Having determined the proportion of cells demonstrating allelic loss for a series of mutated microsatellite markers in a given microdissected sample of pancreatic cancer whether it is derived from pancreatic cyst fluid, cytology cells or tissue resection specimens, it is reasonable to arrange the mutations in a temporal sequence of mutation acquisition. Given that clonal expansion is a driving force leading to replacement of precursor cells with more phenotypically, growth-advantaged, neoplastic cells, mutations acquired earlier in time would be expected to manifest themselves in a larger proportion of cells at a particular tissue target. Allelic loss mutations occurring later in time would be expected to be present in a proportion of cells equal to or less in number than those affected by earlier mutational events. Similarly mutations present at multiple sites across the full extent of a malignant pancreatic cancer could be viewed as having been acquired earlier in time than other mutations present in topographically focal defined areas. By microdissecting the specimen at several points, both the time course and topographic distribution of mutational change can be determined with precision. Earlier mutations affect a larger proportion of cells distributed widely across the specimen. Later mutational events affect a lesser proportion of microdissected cells in a more discrete topographic distribution. This provides the dynamic link between static morphologic pathology and molecular genotyping capable of defining a unique time course of mutation acquisition for a specific patient neoplasm. This hypothesis was then proven for pancreatic cancer and, in particular, fine needle aspiration (FNA) of pancreatic fluid from patients with pancreatic cancer.

Figure 5:
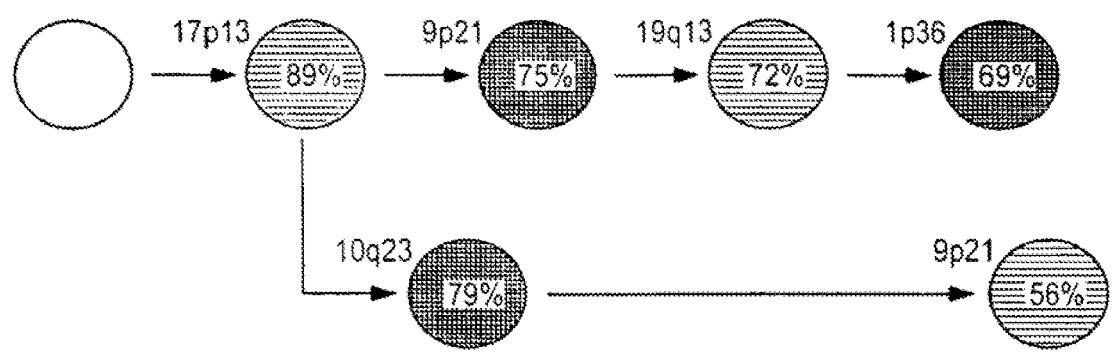
FIG. 5. Temporal sequence of mutation acquisition in an individual patient with pancreatic cancer. Two clones were identified from a single patient-derived from a putative precursor cell undergoing neoplastic transformation with 17p13 allelic imbalance. Allelic imbalance for a particular microsatellite marker with a relative lack of the shorter microsatellite allele is shown in horizontal lines. Allelic imbalance with relative lack of the longer microsatellite allele is shown in vertical lines. The capacity to distinguish between each of the two alleles with respect to relative imbalance is an important property of the genotyping approach as it provides a means to detect different mutational events in topographically separate locations and also temporally separate time in tumor progression. Note that the microsatellite marker for 9p21 shows two independently acquired mutational events affecting alternative alleles with imbalance. This would in turn correspond to a later event in tumorigenesis.

For example, it is possible to convert the tabular information (Table 3) pertaining to the spectrum of acquired mutational damage at different topographic locations within a pancreatic tumor into a temporal sequence of acquired genomic damage and clonal expansion (FIG. 5). Detection of equivalent mutational damage at all sites indicates an early acquired event that has become distributed widely as a result of tumor growth and spread. Such mutations are invariably present in a very high percentage of cells gathered from within individual microdissection targets. Mutations that are present in lesser proportion, but in all targets, indicate later acquisition of the mutation. The presence of mutations focally in only a proportion of microdissection targets indicates even later and focal acquisition in subsets of tumors cells (FIG. 5). Schematic representations can make use of spatial alignment in order to give the diagnosing physician or care giver a simple and direct means to relate to the integrated molecular pathology information.

TABLE 3

Glioma Allelic Imbalance Genotyping of a Pancreatic Adenocarcinoma

| Genomic Location | Microdissection Tumor Target 1 | Microdissection Tumor Target 2 | Microdissection Tumor Target 3 |
|---|---|---|---|
| 1p36a | *69% | *64% | No imbalance |
| 1p36b | Non-informative | Non-informative | Non-informative |
| 1p34 | No imbalance | No imbalance | No imbalance |
| 1p22 | No imbalance | No imbalance | No imbalance |
| 5p11a | Non-informative | Non-informative | Non-informative |
| 5p11b | No imbalance | No imbalance | No imbalance |
| 9p23 | +57% | +66% | No imbalance |

TABLE 3-continued

Glioma Allelic Imbalance Genotyping of a Pancreatic Adenocarcinoma

| Genomic Location | Microdissection Tumor Target 1 | Microdissection Tumor Target 2 | Microdissection Tumor Target 3 |
|---|---|---|---|
| 9p21 | *75% | *70% | +56% |
| 10q23a | Non-informative | Non-informative | Non-informative |
| 10q23b | No imbalance | No imbalance | *79% |
| 17p13a | Non-informative | Non-informative | Non-informative |
| 17p13b | +82% | +77% | +89% |
| 17q23 | No imbalance | No imbalance | +62% |
| 19q13a | +59% | +72% | No imbalance |
| 19q13b | Non-informative | Non-informative | Non-informative |
| 21q23 | No imbalance | No imbalance | No imbalance |

Allelic imbalance for a particular microsatellite marker with relative lack of the shorter microsatellite allele is designated by "*". Allelic imbalance with relative lack of the longer microsatellite allele is designated by "+". The capacity to distinguish between each of the two alleles with respect to relative imbalance is an important property of the genotyping approach, because it provides a means to detect different mutational events in topographically separate locations and temporally separate times in tumor progression. Note that the microsatellite marker for 9p21 shows two independently acquired mutational events affecting alternative alleles with imbalance. This would in turn correspond to a later event in tumorigenesis. See also FIG. 5.

It is clear from the data in Table 3 that the pancreatic cancer has split into two divergent clones, each of which has pursued a separate course of independent temporal mutation acquisition. This is a characteristic of aggressive neoplasms, in that most visceral human cancers manifest a single clone with progressive mutation acquisition.

Although the present invention has been described in detail with reference to examples below, it is understood that various modifications can be made without departing from the spirit of the invention, and would be readily known to the skilled artisan.

EXAMPLES

Example 1

A study was undertaken spanning 19 months from November of 2002 to May of 2004. All patients presenting to Presbyterian University Hospital with a pancreatic cyst were eligible for inclusion. EUS was performed with a Pentax CLA echo-endoscope. Pancreatic cyst aspiration was performed according to clinical need (Wilson Cook NI (22 gauge or 25 gauge needles)) and fluid sent for cytological evaluation and CEA (carcinoembryonic antigen) tumor marker analysis. Intravenous (IV) antibiotics (Levofloxacin, 500 mg) were administered at the time of cyst aspiration.

Cyst aspirate cytology exams were performed in a routine fashion, familiar to the skilled artisan in the medical profession. The primary tissue and fluid targets were from the head of the pancreas. Cytopathologic criteria for malignancy included nuclear enlargement, pleomorphism (minimum of 3 to 4 fold variation in nuclear size), elevated N/C ratio, nuclear membrane irregularity, and coarse chromatin (Solcia, et al., "Tumors of the Pancreas," IN ATLAS OF TUMOR PATHOLOGY, ARMED FORCES INSTITUTE OF PATHOLOGY (American Registry of Pathology, 1995). Cases diagnosed as inconclusive fulfilled some, but not all criteria for malignancy. Less than 1 mL (0.4 mL) of the aspirate was used for the study. DNA analysis was performed as detailed below.

DNA was extracted from the pancreatic fluid by spin column separation (Qiagen, Valencia, Calif.). The spin columns are commercially available and operate on the basis for size discrimination according to manufacturer's instructions. The fluid was centrifuged at the recommended speed. The centrifugal forces cause the fluid containing DNA to cross the membrane which retards and holds back DNA that is beyond a certain minimal base pair length, usually about 70 bases. The DNA captured on the membrane was eluted off and collected in water and the optical density (OD) measured at 260 and 280 nanometer wavelength determination. A higher OD value indicates higher concentration of DNA.

Quantitative PCR was performed using unlabeled oligonucleotide primers with sybr green signal to determine production of double stranded DNA during cycling. Known quantitative controls and replicate microdissection of samples were used to standardize amplification reactions. As a further measure to monitor the effect of allelic imbalance, analyses were performed in replicate genotyping according to the availability of DNA. PCR was carried out in a standard fashion, but can be modified without affecting the application as discussed. Oligonucleotides flanking the microsatellite, single nucleotide polymorphism, or sequence of interest, were prepared based upon known sequence as can be obtained from GenBank. Other sources for genetic sequence information can also be used. The cycling temperatures used were a denaturing step at 95° C. for 30 seconds, followed by annealing at 55° C. for 30 seconds, followed by polymerization at 72° C. for 60 seconds. Other temperature profiles can be used with equal effectiveness. Taq Polymerase Gold was used for DNA polymerization, however, other Taq or similar polymerase enzymes can be substituted.

One-microliter aliquots of pancreatic cyst aspirate were used in a polymerase chain amplification reaction (PCR) as described above for a broad panel of tumor suppressor genes commonly involved in human pancreatic carcinogenesis. Tables 4 and 5 provide the panel of mutations used in the study. K-ras-2 gene and details on tumor suppressor genes (with associated markers) and chromosomal location and mutation type are provided. Other microsatellite markers or gene/genomic targets can be substituted with equal effectiveness.

TABLE 4

| MARKER | CYTOGENETIC LOCATION | PROXIMITY TUMOR SUPPORESSOR GENE |
|---|---|---|
| D1S407 | 1p36 | UNKNOWN |
| D1S1193 | 1p36 | UNKNOWN |
| LMYC | 1p34 | UNKNOWN |
| D1S1172 | 1p22 | UNKNOWN |
| D3S1539 | 3p25 | VHL |
| D3S2303 | 3p26 | OGG1 |
| D5S592 | 5q23 | APC |

Tumor suppressor gene LOH was determined by analysis of tightly linked, informative polymorphic microsatellites. Use of two markers within each locus was used to increase the likelihood that at least one of the markers would be polymorphic within a subject, and thus informative for LOH analysis.

PCR amplification was designed to generate amplicons of less than 200 base pairs long using synthetic oligonucleotide primers flanking each microsatellite. Oligonucleotide primers were created with 5' fluorescent moieties (i.e., FAM, HEX, NED) suitable for automated fragment analysis. The PCR products were analyzed by capillary electrophoresis using an ABI 3100 system according to manufacturer's instructions (Applied Biosystems, Foster City, Calif.). Allele peak heights and lengths were used to define the presence or absence of allelic imbalance (i.e., LOH) for a given sample. Allelic imbalance was reported when the ratio of polymorphic allelic bands for a particular marker was beyond 95% confidence limits for the variation in peak heights for individual allele pairings derived from analysis using non-neoplastic specimen samples. In general, this value was below 0.5 or above 2.0 (Rolston, et. al., *J. Mol. Diagn.* 2001, 3: 129-32). DNA sequencing of K-ras-2 exon 1 PCR amplified DNA was used to search for and characterize point mutations in codons 12 and 13.

Allelic imbalance mutations were treated as genomic deletions associated with tumor suppressor genes. The ratio of allele peak heights is a measure of the admixture of mutated and non-mutated cells or DNA, and varies according to the individual pairing of specific microsatellite marker alleles. Allele ratios of about 2.0 or about 0.5 were said to be present when 50% of the total DNA was derived from cells possessing the loss. The deviation from ideal normal ratio of about 1.0 indicated which specific allele was affected. Similarly, allele ratios below about 0.5 or above about 2.0 could be mathematically correlated with the proportion of cells affected by a genomic loss. The order of mutation acquisition is then arranged in a temporal sequence of mutation accumulation reflecting the proportion of cells affected by specific microsatellite marker loss. Markers displaying more extreme ratios (below 0.5 or above 2.0) are considered to have been acquired earlier. Assuming a model of allelic loss with minimal non-neoplastic cell DNA inclusion, the percentage of mutated DNA was determined for each marker. When two or more mutations (i.e., K-ras-2 and/or allelic imbalance mutations) were detected, their time course of accumulation was inferred by the proportion of total DNA manifesting the alteration. In the case of K-ras-2 oncogene point mutation, involvement of 100% of cells was considered to be present when the density of the mutated base using sequencing autoradiography was equal to or greater than the normal sequence base pair. This was determined qualitatively by visual comparison. This can also be performed quantitatively in the same manner using automated fluorescent capillary gel electrophoresis, for example.

Continuous variables were presented as mean±standard deviation (SD). Differences across groups were compared using a one-way analysis of variance. Multiple comparisons were adjusted using the post-hoc Bonferroni test. In cases where the variance across groups was not homogenous, as assessed by the Levene statistic, data was analyzed using a non-parametric analysis of variance or the Kruskal Wallis test. If this was significant, further, hypothesis driven two-group, non-parametric comparisons were undertaken using the Mann-Whitney U test. A two-tailed p-value of <0.05 was considered significant. Sensitivity and specificity were calculated as appropriate. Data were analyzed using the statistical package, SPSS version 12.0 for Windows (SPSS Inc., Chicago Ill.).

Results

Thirty-three patients with pancreatic cysts were eligible for analysis. This was based on the presence of final surgical pathology (27 cases) or cytological proven cancer from the fine need aspirate (FNA) sample (5 cases). Eleven cystic lesions were malignant (8 invasive cancer, 3 carcinoma-in-situ), 14 were premalignant (10 focal borderline histology, 5 no dysplasia), and 8 cystic lesions were benign (6 pseudocysts, 1 lymphoepithelial cyst, 1 mesothelial cyst). The results are provided in Table 6 and discussed below.

Five malignant cysts were diagnosed as malignant due to the presence of unequivocally malignant cells upon cytological evaluation of the FNA of an associated solid component in the cyst. These patients were not deemed surgical candidates and therefore pathological confirmation is not available. Three cysts with invasive cancer and 3 with carcinoma-in-situ underwent surgery. Of these only 1 cyst was diagnosed as malignant on the basis of cytology. This group of 6 cases was composed of 4 IPMN and 2 mucinous cystadenocarcinomas.

There were 10 IPMN and 4 mucinous cystadenomas in the premalignant category. FNA cytology evaluation of only one premalignant cyst was diagnostic for a low-grade mucinous cystic neoplasm. Two premalignant cysts had inconclusive cytology and the others (11 cysts) had negative cytology. The 8 benign cysts had inconclusive cytology in one and a negative cytology evaluation in 7 cysts.

Figure 3A:
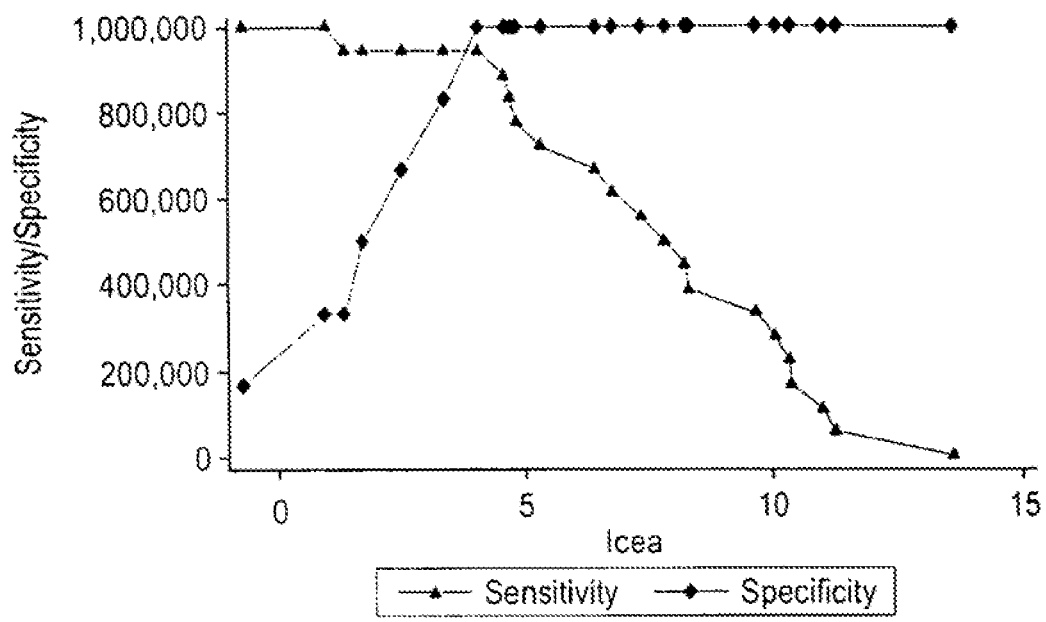
FIGS. 3A and B. The top graph (FIG. 3A) presents the ROC comparing the log value of cyst CEA level for mucinous and benign cysts. The bottom graph (FIG. 3B) presents the ROC comparing the log value of cyst CEA level for malignant and premalignant mucinous cysts.
Figure 3B:
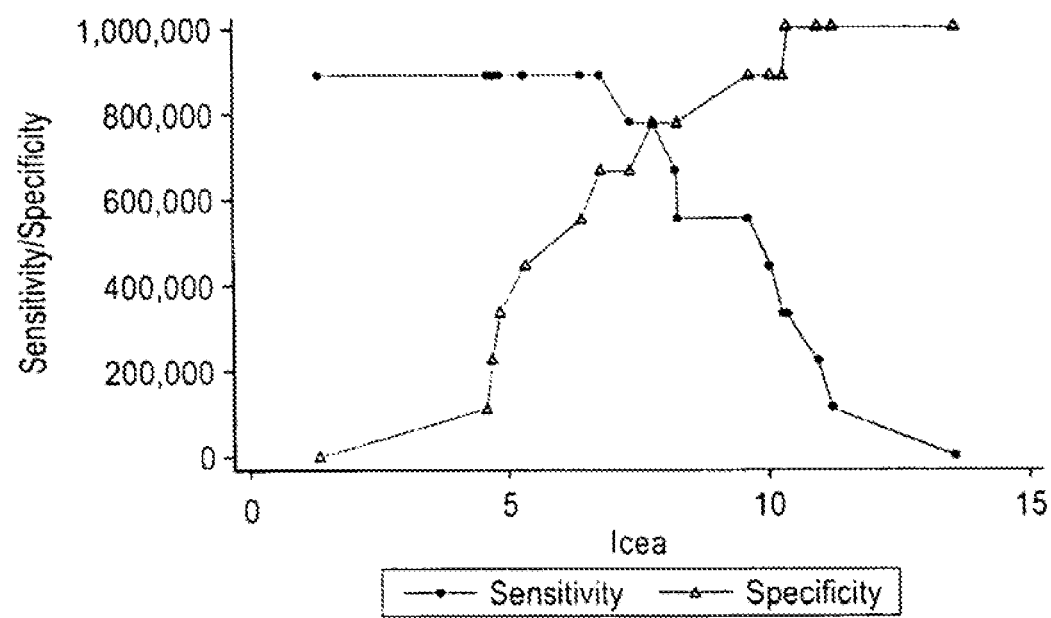

Cyst CEA level was available in 24 cases (9 malignant, 9 premalignant, and 6 benign cysts). Cyst fluid CEA analysis could not be performed in the other 9 cases due to insufficient fluid to run the test. Mean CEA level for the benign group is 17.7 (STD+/−21.7) [95% CI 5.0 to 40.5], for the premalignant group is 5774 (STD+/−10984) [95% CI 2668 to 14217], and for the malignant group was 108360 (STD+/−251860) [95% CI 85236 to 301957]. This difference was significant between the benign and premalignant groups (p=0.001) and the premalignant and malignant groups (p<0.05). Due to considerable overlap and extreme values, receiver-operator-curves were generated for the log value of the CEA. A CEA level of 42 corresponded to a sensitivity and specificity of 94% to differentiate between benign cysts and MCN. A CEA level of 2320 yielded a sensitivity and specificity of 78% to differentiate between malignant and premalignant cysts. See FIGS. 3A and B.

Figure 4A:
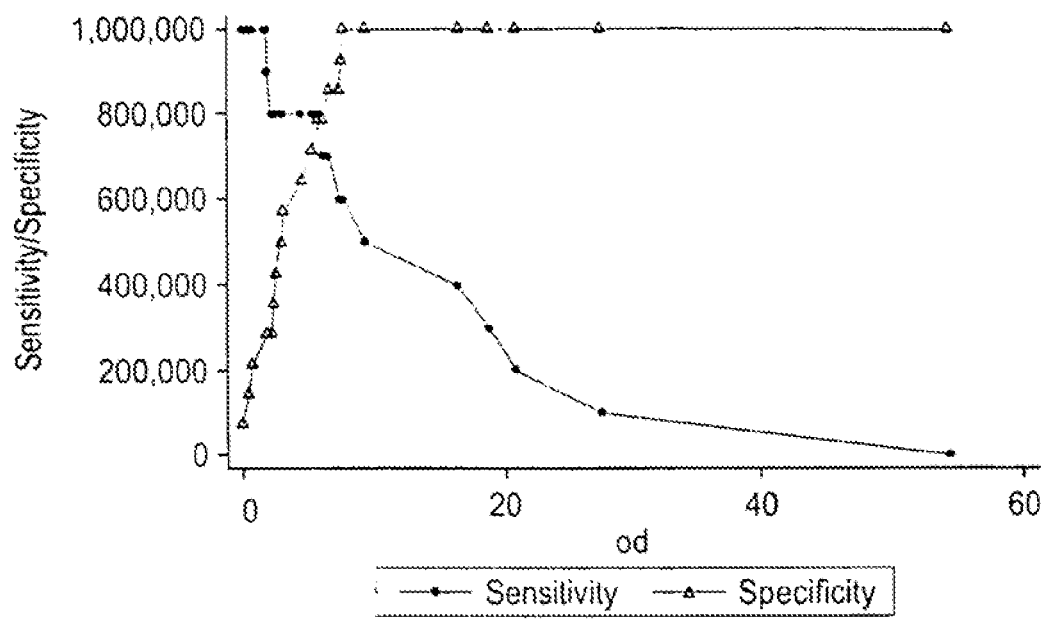
FIGS. 4A and B. The top graph (FIG. 4A) presents the ROC comparing the cyst aspirate OD level for malignant and premalignant mucinous cysts. The bottom graph (FIG. 4B) presents the ROC comparing the cyst aspirate quantitative PCR (qPCRcycle#) for malignant and premalignant mucinous cysts.

The OD was available on 32 cyst aspirates. Mean OD for the 3 groups is as follows: benign 6.5 (STD+/−5.9) [95% CI 1.5 to 11.4], premalignant 3.7 (STD+/−2.6) [95% CI 2.2 to 5.2], and malignant group 16.5 (STD+/−15.7) [95% CI 5.2 to 27.8]. See FIG. 4A. The difference between the premalignant and malignant group was significant (p=0.008). An OD value of 7 yielded 80% sensitivity and specificity respectively for the presence of malignancy in a mucinous cystic neoplasm. Table 2 provides data pertaining to the pathology (final diagnosis), cytology results, aspirate CEA level, OD, quantitative PCR cycle (qPCR cycle), and the sequence of mutations for all cysts included in the study.

Figure 4B:
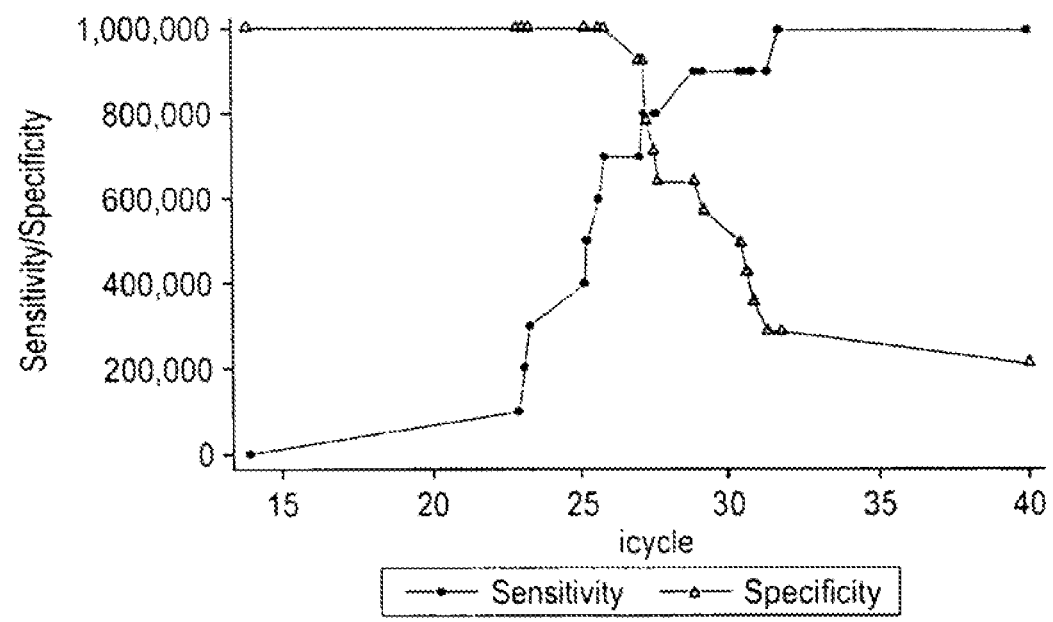

The test of DNA quality or amplifiable DNA (quantitative PCR) as presented by the mean qPCRcycle# for the 3 groups was available for 27 cysts. See FIG. 4B. In 5 cysts (3 premalignant and 2 benign), there was no amplifiable DNA into 40 cycles on the qPCR and hence was assumed to be 40 for sake of analysis. One malignant sample did not undergo qPCR. The results are as follows: benign 33 (STD+/−4.9) [95% CI 28.9 to 37], premalignant 31.2 (STD+/−5) [95% CI 28.3 to 34.1], and malignant group 24.5 (STD+/−4.5) [95% CI 21.3 to 27.8]. This difference was significant for the benign and malignant group (Bonferroni p=0.003) and the premalignant and malignant group (Bonferroni p=0.007). A qPCRcycle# of 27 yielded a sensitivity and specificity of 80% for the presence of malignancy in a mucinous cystic neoplasm.

Mutational analysis (LOH and K-ras point mutation) was available on all cyst aspirates. No mutations were detected in any of the 8 cysts in the benign group. Six of 14 cysts in the premalignant group carried mutations. One patient with 2 cysts (IPMN and counted as 1 case for the analysis) had an identical K-ras mutation followed by separate allelic losses. The mean number of mutations for the premalignant group is 0.9 (STD+/−1.2) [95% CI 0.2 to 1.6]. Ten of the 11 malignant cysts carried multiple mutations. No mutations were detected in one cyst with HGD. The mean number of mutations in the malignant group is 2.8 (STD+/−1.3) [95% CI 1.9 to 3.7]. The number of mutations differed significantly between the malignant and premalignant (p=0.003), malignant and benign (p<0.001), and premalignant and benign categories (p=0.036).

The sequence of mutation accumulation was significantly different between the premalignant and malignant categories. All cysts with invasive cancer and 2 of 3 cysts with HGD had first acquired a K-ras mutation followed by allelic loss. In contrast, 2 of 14 premalignant cysts acquired a K-ras mutation as the first step of DNA damage. Of these, only 1 cyst had an additional allelic loss. The occurrence of K-ras point mutation first with or without subsequent allelic loss was significantly associated with a malignant cyst (p<0.001). The sensitivity and specificity of a K-ras mutation occurring as the first hit was 91% and 86% respectively, for the presence of malignancy in a mucinous cystic neoplasm. The presence of allelic loss following K-ras mutation yielded a sensitivity of 91% and specificity of 93%, for the presence of malignancy in a mucinous cystic neoplasm.

A cyst aspirate CEA level of 42 yielded a much higher sensitivity and specificity value on the receiver operator curves (94% compared to 79%). This maybe due to lack of uniformity across laboratories measuring CEA levels with different assays. Cyst aspirate CEA level also appeared to predict the presence of early malignancy with moderate accuracy (sensitivity and specificity less than 80% for a CEA level of 2320), although confounded by extreme values. Nevertheless, the overwhelming evidence speaks for the presence of low or borderline amounts of intact DNA in low grades forms of DNA. Cytological analysis of pancreatic cysts in the absence of a solid component remained insensitive, reflecting the sparse number of cells in cyst aspirates and the subjectivity of the evaluation.

One aspect of the present invention involves the initial evaluation of the presence and quality of DNA followed by DNA mutational analysis. Benign pancreatic cysts (e.g., pseudocysts) and low grade MCN have a low rate of cellular turnover and by extension scant cyst fluid DNA. In contrast, malignant PCN should have uncontrolled cell growth and constant release of high quality, albeit mutated, DNA into the cyst fluid bathing the malignant lining. This is apparent from the results showing significantly different cyst aspirate OD and qPCR cycle values for the malignant and non malignant categories.

After the presence and cumulative amount of mutational damage in pancreatic cyst fluid was defined, the temporal sequence of individual mutation acquisition was inferred. The time course derived from analysis of the cyst fluid was compared to that derived from genotyping microdissected tissue samples from the pancreatic resection specimen. Table 7 provides the mutation acquisition pattern of four selected malignant specimens. The middle column provides the mutation sequence in microdissected tissue from the surgical specimen (first 3 cases) or from a positive cytology slide prepared from FNA of a solid component of a malignant cyst. The right column provides the mutation sequence from the corresponding cyst fluid aspirate. A near perfect correlation with respect to time course of mutational acquisition was found for the earlier occurring mutations, strongly supporting the validity of these methods used to detect and characterize mutational change. K-ras-2 point mutational change was noted as a first event followed by allelic loss in all patients but one ultimately demonstrated to have a malignant MCN. Only one patient in the premalignant group exhibited this pattern. This pattern of mutational damage was found to be very sensitive and specific for the presence of malignancy in MCN (91% and 93% respectively). Prior studies in brushings of malignant biliary strictures (GUT) also report the presence of this degree of mutational damage to be supportive of the presence of cancer.

TABLE 5

| Gene | Mutation Type | Locus | Microsatellite Marker | Genebank Reference |
|---|---|---|---|---|
| K-ras | Point mutation | 12p12 | | |
| CMM/RIZ | Deletion | 1p36-1p34 | D1S407 | L18040 |
| | | | MYCL | M19720 |
| VHL | Deletion | 3p26-3p25 | D3S1539 | L16393 |
| | | | D3S2303 | L17972 |
| APC | Deletion | 5q23-5q23 | D5S592 | L16423 |
| | | | D5S615 | L18737 |
| P16 | Deletion | 9p21-9p23 | D9S251 | L18726 |
| | | | D9S254 | L18050 |
| PTEN | Deletion | 10q23-10q23 | D10S520 | L16357 |
| | | | D10S1173 | L30341 |
| P53 | Deletion | 17p13-17p13 | D17S974 | G07961 |
| | | | D17S1289 | G09615 |

TABLE 6

| OBSERVATION | PATHOLOGY | CYTOLOGY | CEA | OD | qPCRcycle# | MUTATIONS |
|---|---|---|---|---|---|---|
| 1 | MCAC | Positive | 58960 | | 25.2 | kras-9p,9p-17p,17p |
| 2 | Malignant | Positive | 77600 | 20.95 | | kras-1p-1p |
| 3 | IPMN/CA | Inconclusive | 3.8 | 1.9 | 27.1 | kras-10q-9p-5q |
| 4 | Malignant | Positive | 23000 | 27.7 | 25.3 | kras-9p-1p |
| 5 | Malignant | Positive | 4080 | 16.5 | 25.7 | kras-17p-1p-5q |
| 6 | Malignant | Positive | | 2.25 | 13.9 | kras-5q |
| 7 | Malignant | Inconclusive | 776000 | 18.9 | 23.3 | kras-9p-17p |
| 8 | MCAC | Inconclusive | 30150 | 9.3 | 22.9 | kras-1p |
| 9 | IPMN/HGD | Negative | 3871 | 7.45 | 31.4 | kras-9q-5q |
| 10 | IPMN/HGD | Inconclusive | | 54.3 | 23.1 | No mutation |
| 11 | IPMN/HGD | Negative | 1580 | 6.1 | 27.7 | K-ras-10q |
| 12 | IPMN | Negative | 2550 | 5.8 | 27.2 | K-ras-17p/3p |
| 13 | IPMN | Positive | 98 | 6.6 | 29 | K-ras |
| 14 | MCA | Inconclusive | 15492 | 5.4 | 30.9 | No mutation |
| 15 | MCA | Negative | 109 | 7.55 | 25.9 | 5q-kras-1p |
| 16 | MCA | Negative | 31900 | 3.1 | 30.5 | 3p-kras |
| 17 | IPMN | Inconclusive | 879 | 0.4 | 40 | No mutation |

TABLE 6-continued

| OBSERVATION | PATHOLOGY | CYTOLOGY | CEA | OD | qPCRcycle# | MUTATIONS |
|---|---|---|---|---|---|---|
| 18 | IPMN | Negative | 203 | 1.8 | 31.8 | No mutation |
| 19 | MCA | Negative | 614 | 2.4 | 27.3 | 3p-1p |
| 20 | IPMN | Negative | 126 | 3.05 | 29.3 | No mutation |
| 21 | IPMN | Negative |  | 2.6 | 27.6 | No mutation |
| 22 | IPMN | Negative |  | 7.7 | 27.2 | No mutation |
| 23 | IPMN | Negative |  | 4.55 | 30.7 | 5q-1p-10q |
| 24 | IPMN |  |  | 0.8 |  | No mutation |
| 25 | IPMN |  |  |  |  | No mutation |
| 26 | Lymphoepithelial cyst | Negative |  | 14.4 | 29.4 | No mutation |
| 27 | Pseudocyst | Negative | 56.8 | 14.8 | 27.2 | No mutation |
| 28 | Pseudocyst | Negative |  | 2.5 | 30.1 | No mutation |
| 29 | Pseudocyst | Negative | 5.5 | 1.8 | 29.8 | No mutation |
| 30 | Pseudocyst | Negative | 2.6 | 1.2 | 40 | No mutation |
| 31 | Pseudocyst | Negative | 12.1 | 1.2 | 32.4 | No mutation |
| 32 | Pseudocyst | Negative | 28.8 | 10.7 | 40 | No mutation |
| 33 | Mesothelial cyst | Inconclusive | 0.5 | 5.4 | 40 | No mutation |

TABLE 7

| PATHOLOGY | PATH MUTATION-ORDER | ASPIRATE MUTATION-ORDER |
|---|---|---|
| Mucinous Cystadenocarcinoma | kras-9p, 9p-17p, 17p-9q-1p | kras-9p, 9p-17p, 17p |
| Mucinous Cystadenocarcinoma | kras-9p-17p-3p | kras-9p-17p |
| IPMN with high grade dysplasia | kras-9q-9p-5q-17p | kras-9q-5q |
| Mucinous Cystadenocarcinoma | kras-1p-10q-5q | kras-1p |

Example 2

An interesting observation, consistently displayed by most metastatic neoplasms, is the preservation of the time course of mutation acquisition in metastatic deposits of tumor (FIG. 6, Table 8). In this representative example, a pancreatic carcinoma was associated with an isolated recurrence of cancer in the lip after a two year latency interval. The possibility of new primary occurrence was considered in view of the unusual location for metastatic spread (i.e., to the lip). No other tumor deposits were noted in the patient. The pancreatic and lip neoplasms were each microdissected at two sites within each specimen. Tissue microdissection was designed to capture purified representative cellular samples of each tumor deposit in pancreas and in lip. Tissue microdissection was performed manually using a scalpel under stereomicroscopic observation (Olympus SZ-PT). The neoplasms were found to be highly concordant with respect to the specific markers and alleles affected by mutational genomic loss (Table 8). These findings by themselves are sufficient to affirm the primary and metastatic relationship between the lip and pancreatic tumors in this patient. Of note, however, was the identical temporal profile of mutational damage. Specifically, both specimens had equivalent proportions of tumor cells bearing specific deletions in primary and metastatic deposits (Table 8).

TABLE 8

Microdissection Genotyping Tumor Metastasis Versus Secondary Primary Formation

| Genomic Location | Microdissect Normal Target Pancreas | Microdissect Tumor Target 1 Pancreas | Microdissect Tumor Target 2 Pancreas | Microdissect Tumor Target 1 Lip | Microdissect Tumor Target 2 Lip |
|---|---|---|---|---|---|
| 1p36a | No imbalance | No imbalance | No imbalance | No imbalance | No imbalance |
| 1p36b | Noninform | Noninform | Noninform | Noninform | Noninform |
| 1p34 | No imbalance | No imbalance | No imbalance | No imbalance | No imbalance |
| 3p26 | No imbalance | *77% | *69% | *73% | *72% |
| 3p25 | Noninform | Noninform | Noninform | Noninform | Noninform |
| 5q23a | No imbalance | No imbalance | No imbalance | No imbalance | No imbalance |
| 5q23b | Noninform | Noninform | Noninform | Noninform | Noninform |
| 9p23 | No imbalance | +62% | +65% | +53% | +59% |
| 9p21 | No imbalance | +55% | +62% | +62% | +63% |
| 9q23 | No imbalance | *54% | No imbalance | *56% | *51% |
| 10q23a | No imbalance | No imbalance | No imbalance | No imbalance | No imbalance |
| 10q23b | No imbalance | No imbalance | No imbalance | No imbalance | No imbalance |
| 17p13a | Noninform | Noninform | Noninform | Noninform | Noninform |
| 17p13b | No imbalance | No imbalance | No imbalance | No imbalance | No imbalance |
| 17q23 | No imbalance | No imbalance | No imbalance | No imbalance | No imbalance |
| 21q23 | No imbalance | *91% | *89% | *87% | *92% |
| 22q12 | No imbalance | No imbalance | No imbalance | No imbalance | No imbalance |

Allelic imbalance for a particular microsatellite marker with relative lack of the shorter microsatellite allele is designated by a "*". Allelic imbalance with relative lack of the longer microsatellite allele is shown by a "+". The capacity to distinguish between each of the two alleles with respect to relative imbalance is an important property of the genotyping approach, because it provides a means to detect different mutational events in topographically separate locations and also temporally separate times in tumor progression.

If metastatic seeding was to have clonally evolved from a single pancreatic carcinoma cell circulating via the bloodstream and implanting in the lip, then all mutations acquired prior to the seeding event would be expected to be present in all cells of the lip metastasis. This is in fact not the case but rather the metastasis recapitulates the temporal sequence of mutation acquisition of the primary tumor (Table 8). This can be accounted for in several ways, but the most likely is metastatic spread not of a single cells but rather a collection of cells sufficiently large to demonstrate the mixture of remote and recently acquired mutations in the primary tumor. This suggests that an important event in metastatic seeding is the creation of a circulating pool of tumors cell clusters of sufficient size to survive implantation and growth in the metastatic site. It is proposed that these larger cell clusters possess growth advantages compared to circulating, single cells. These observations support the ability to delineate the time course of mutation acquisition in human cancer based on topographic genotyping.

These concepts were then applied to pancreatic cyst fluid analysis (Table 9-11). The order of mutation acquisition was inferred based on a clonal expansion model for carcinogenesis, in which acquired mutations are causally associated with phenotypic overgrowth of precursor cells as described above. Two equivalent aliquots of pancreatic cyst fluid DNA showing 90% and 50% mutated DNA respectively for two specific markers could then be arranged in an inferred temporal sequence, in which the 90% mutation preceded the 50% mutation. This inference recognizes that individual neoplasms may exhibit multiple independent clonal populations and that regression of individual clones may affect the inference. However, in preliminary studies based on microdissection of pancreatic cancer, both of these were shown to be of minimal impact with respect to the dominant growing pancreatic neoplasm. Markers displaying more extreme ratios are considered to have been acquired earlier, based on the premise of clonal expansion enabling tumor cell populations to progressively replace each other when mutations causally associated with increasing malignant phenotype had occurred. Assuming a model of allelic loss with minimal non-neoplastic cell DNA inclusion, the percentage of mutated DNA was determined for each marker. This provided the basis for inferred temporal sequence determination of multiple mutations when such was present.

Determination of the k-ras-2 point mutation was accomplished by fluorescent based direct sequencing of the amplified first exon of the gene. This is accomplished by dideoxychain termination cycle sequencing using fluorescent labeled chain termination molecules. The molecules are then separated using capillary electrophoresis according to manufacturer's recommended instructions (Applied Biosystems, ABI 3100; Mountainview, Calif.). The sensitivity of point mutation detection has been shown in this system to be at least 15% mutated cells. In the case of k-ras-2 oncogene point mutation, involvement of 100% of cells was considered to be present when the fluorescent peak height of the mutated base on sequencing was equal to or greater than the normal sequence base. Since k-ras-2 point mutation need only affect one allele, 100% microdissected cell involvement was considered to be present when normal and mutant peak heights were equal.

Example 3

Additional experiments were performed to validate the approach of calculating the mutation acquisition pattern from the ratio of allele peak heights on electropherograms. These involved 17 cases of bile duct cancer and pancreatic cancer with cytologic and surgical specimens previously studied for microdissection based genotyping (Table 9). The methodology is similar, it involves obtaining and analyzing multiple cells clusters from different parts of the tumor (cytology and surgical pathology) for k-ras point mutation and microsatellite loss analysis. The LOH analysis utilized fluorescent capillary electrophoresis. Allelic imbalance analysis is based on the use of fluorescent labeled primers (HEX, TET, FAM, and TAMRA) during PCR amplification. The primer labeled molecules are then separated by capillary electrophoresis according to manufacturer's recommendations (Applied Biosystems, ABI 3100; Mountainview, Calif.). The temporal sequence for each patient was calculated as discussed above from the ratios of the peak heights on the electropherograms. The greater the degree of imbalance (i.e., ratio values approaching either zero or infinity), the greater the proportion of microdissected cells affected by this form of mutational damage. The lesser the degree of significant imbalance (i.e., ratio values exceeding but closer to the thresholds defined as two standard deviations above or below the average for allele ratios using microdissected non-neoplastic tissue samples) the lesser proportion of microdissected cells affected by this marker mutation. Based on the model of clonal expansion, markers with greater degrees of allelic imbalance were acquired earlier in tumorigenesis than markers exhibiting lesser degrees of imbalance derived for the same microdissected cell population. The calculated temporal sequence was compared between the different microdissected cell clusters for each case. The first and second mutation/loss from the different cytologic and surgical topographic areas was identical in all 17 cases. Eleven cases had more than 2 mutation/losses, and the third microsatellite loss for all of these as calculated from the electropherograms was concordant between different microdissected samples of each tumor. The fourth microsatellite loss in 5 tumors was concordant in 4 out of 5 tumors. Cytology samples from 2 tumors carried additional microsatellite losses not seen in the microdissected surgical specimen. Surgical specimens from 6 tumors carried additional microsatellite losses not seen in the corresponding cytology specimens. These were all assessed as having occurred later in time based on calculation from the electropherograms. Based on this data, the following was concluded:

1) Mutation acquisition pattern/microsatellite loss timing calculated from peak heights on electropherograms is a valid approach especially for mutations occurring early in the process of tumorigenesis.
2) Later mutations that are not common to all topographic sites in a tumor account for intra-tumoral heterogeneity.

TABLE 9

Comparative Analysis of Time Course Determination in Pancreaticobiliary Brush Cytology and Corresponding Resected Tumor Specimens

| PT# | TIME COURSE AS DETERMINED USING ENDOSCOPIC RETROGRADE PANCREATICOBILIARY BRUSHING | TIME COURSE AS DETERMINED USING MICRODISSECTED TISSUE SAMPLES OF PANCREATIC AND BILIARY ADENOCARCINOMA |
|---|---|---|
| 1 | *k-ras-2/12D, *1P36, *9P21, *17P13, 3P26 | *k-ras-2/12D, *1P36, *9P21, *17P13, 3P26 |
| 2 | *k-ras-2/12R, *17P13, *1P36, 10Q23, 3P26 | *k-ras-2/12R, *17P13, *1P36, 10Q23, 3P26 |
| 3 | *k-ras-2/12R, *9P21, *3P26, 5Q23, 1P36 | *k-ras-2/12R, *9P21, *3P26, *17P13, *5Q23, 1P36 |
| 4 | *k-ras-2/12V, *5Q23, 3P26 | *k-ras-2/12V, *5Q23, *3P26 |
| 5 | †10Q23, †17P13, †3P26 | †10Q23, †17P13, †3P26 |
| 6 | †10Q23, †17P13, †3P26 | †10Q23, †17P13, 3P26 |
| 7 | †9P21, †17P13, †5Q23, 3P26 | †9P21, †17P13, †5Q23, 3P26 |
| 8 | †1P36, †5Q23, †10Q23, 3P26 | †1P36, †5Q23, †10Q23 |
| 9 | †10Q23, †9P21, †5Q23 | †10Q23, †9P21, †5Q23, 1P36 |
| 10 | †17P13, †9P21 | †17P13, †9P21, 3P26 |
| 11 | †1P36, †9P21 | †1P36, †9P21, †5Q23, 10Q23 |
| 12 | †17P13, †3P26 | †17P13, †3P26, †9P21, 1P36 |
| 13 | *10Q23, *9P21, 5Q23, 3P26 | *10Q23, *9P21, 5Q23 |
| 14 | †5Q23, †1P36 | †5Q23, †1P36 |
| 15 | †1P36, †10Q23 | †1P36, †10Q23, 17P13 |
| 16 | †9p21, †1p36 | †9p21, †1p36 |
| 17 | *k-ras-2/12D, *9p21, *5q23, *10q23 | *k-ras-2/12D, *9p21, *5q23, *10q23 |

"*"denotes pancreatic cancer in which degree of allelic imbalance (LOH) or oncogene point mutation is greater than 75% of cellular DNA constituting early acquired mutations.
"†"denotes bile duct cancer in which degree of allelic imbalance (LOH) oncogene point mutation is greater than 75% of cellular DNA constituting early acquired mutations.

The mutations discussed in Table 9 above are arranged from left to right in decreasing order of tumor cell content corresponding to temporal sequence of mutation acquisition. Mutations without either "*" or "†" involve less than 75% of the cellular DNA.

The sequence of mutation accumulation was significantly different between the premalignant and malignant categories. All cysts with invasive cancer and 2 of 3 cysts with high grade dysplasia (HGD) had acquired a k-ras mutation first, followed by allelic loss (Table 10). In contrast, 2 of 14 premalignant cysts acquired a k-ras mutation as the first step of DNA damage. Of these, only 1 cyst had an additional allelic loss. The occurrence of the k-ras point mutation first, with or without subsequent allelic loss, was significantly associated with a malignant cyst (p<0.001). The sensitivity and specificity of a k-ras mutation occurring as the first hit was 91% and 86% respectively, for the presence of malignancy in a mucinous cystic neoplasm. The presence of allelic loss following k-ras mutation yielded a sensitivity of 91% and specificity of 93%, for the presence of malignancy in a mucinous cystic neoplasm (Table 8). "Sensitivity" as used in this example refers to the proportion of patients who were found to have high grade dysplasia and/or adenocarcinoma who demonstrated the presence of mutational change (+ test). "Specificity" as used in this example is the proportion of patients who did not have high grade dysplasia and/or adenocarcinoma and who demonstrated no detectable mutational change (− test).

TABLE 10

| PATHOLOGY | PATIENTS | CEA | OD | CT | NUMBER OF MUTATIONS | K-RAS FOLLOWED BY LOH |
|---|---|---|---|---|---|---|
| MALIGNANT AND HGD | 11 | 108360 +/− 251860 | 16.5 +/− 15.7 | 24.5 +/− 4.5 | 2.8 +/− 1.3 | 10/11 |
| PRE-MALIGNANT | 15 | 5237 +/− 10494 | 3.6 +/− 2.5 | 30.9 +/− 5 | 0.9 +/− 1.2 | 1/15 |
| P VALUE | | 0.034 | 0.008 | 0.009 | 0.002 | <0.001 |
| SENSITIVITY & SPECIFICITY | | CEA = 2320 78% | OD = 7 80% | CT = 27 80% | MUTATION = 3 SENS = 78% SPEC = 75% | SENS = 91% SPEC = 93% |

Table 10 provides summary data and performance characteristics of the aspirate CEA level, OD, quantitative PCR cycle # (CT) and the number and sequence of mutations for the premalignant and malignant cysts.

In selected patients where surgical resection specimens were available for comparative genotyping, the time course of mutation acquisition derived from the cyst fluid was proven correct by microdissecting the resected pancreatic tissue (Table 11).

TABLE 11

| PATHOLOGY | PATH MUTATION-ORDER | ASPIRATE MUTATION-ORDER |
|---|---|---|
| MUCINOUS CYSTADENOCARCINOMA | kras-9p, 9p-17p, 17p-9q-1p | kras-9p, 9p-17p, 17p |
| MUCINOUS CYSTADENOCARCINOMA | kras-9p-17p-3p | kras-9p-17p |
| MUCINOUS CYSTADENOCARCINOMA | k-ras-1p-10q-5q + 1 | k-ras-1p34 |
| IPMN WITH HIGH GRADE DYSPLASIA | kras-9q-9p-5q-17p | kras-9q-5q |

Table 11 provides the mutation acquisition pattern of four selected malignant specimens. The center column of Table 11 provides the mutation sequence in microdissected tissue from the surgical specimen (first 3 cases) or from a positive cytology slide prepared from a FNA of a solid component of a malignant cyst. The right column provides the mutation sequence from the corresponding cyst fluid aspirate obtained from the patient.

These studies validate the technique of topographic genotyping to establish the time course of mutation acquisition and that this value is biological relevant in its ability to predict tumor aggressiveness.

All references cited herein are incorporated herein in their entirety for all purposes. Priority is claimed to U.S. Provisional Application Nos. 60/620,926; 60/631,240; 60/644,568; 60/679,968; and 60/679,969 filed respectively on Oct. 22, 2004; Nov. 29, 2004; Jan. 19, 2005; May 12, 2005, and May 12, 2005, which are incorporated herein in their entirety for all purposes. Applicants also incorporate herein in their entirety for all purposes the U.S. applications entitled "Enhanced Amplifiability of Minute Fixative-Treated Tissue Samples, Minute Stained Cytology Samples, and Other Minute Sources of DNA", "Molecular Analysis of Cellular Fluid and Liquid Cytology Specimens for Clinical Diagnosis, Characterization, and Integration with Microscopic Pathology Evaluation", and "Dynamic Genomic Deletion Expansion and Formulation of Molecular Marker Panels for Integrated Molecular Pathology Diagnosis and Characterization of Tissue, Cellular Fluid, and Pure Fluid Specimens" filed Oct. 24, 2005.

We claim:

1. A method for predicting the presence of a pancreatic anomaly in a patient suffering from pancreatic cysts comprising:
   a) performing molecular analysis of DNA from an aspirate from a patient pancreatic cyst comprising
      (i) performing an optical density analysis of the aspirate to determine DNA quantity;
      (ii) performing a quantitative PCR analysis of the aspirate to determine DNA quality;
      (iii) performing competitive template PCR to determine DNA quality; and
   b) performing mutation analysis of the DNA in the aspirate comprising:
      (i) determining the presence of mutations in D1S407, D1S1193, LMYC, D1S1172, D3S1539, D3S2303, or D5S592;
      (ii) determining tumor suppressor gene loss of heterozygosity (LOH) by analyzing polymorphic microsatellites or other polymorphic markers linked to tumor suppressor genes with respect to their allelic balances, wherein the tumor suppressor genes are selected from the group consisting of: VHL, APC, P53, PTEN, and P16;
      (iii) determining point mutations in the K-ras oncogene and/or point mutations in at least one other cancer-associated gene;
      (iv) determining other structural alterations in the DNA;
      (v) determining the percentage of mutated DNA from steps b)(ii) and b)(iii); and
      (vi) determining the specific temporal sequence of mutation accumulation based on step (v), wherein the temporal sequence of mutation accumulation is predictive of the presence of a pancreatic anomaly.

2. The method of claim 1, further comprising confirming the results of steps (a) and (b) by comparing said results with a pathologic analysis of a cystic lesion surgically obtained from the patient.

3. The method of claim 1, further comprising analyzing the cyst carcinoembryonic antigen (CEA) level of the aspirate.

4. The method of claim 1, wherein the DNA in the aspirate is free floating, or free and adherent to the surface of cells or tissue constituents of the cyst.

5. The method of claim 1, wherein the cycles of quantitative PCR performed in step a)(ii) is greater than a threshold unique for that specific type of DNA.

6. The method of claim 1, wherein the patient is a mammal.

7. The method of claim 6, wherein the patient is a human.

8. The method of claim 1, wherein the pancreatic anomaly is a pancreatic cancer or dysplasia, pre-cancerous pancreatic state, or non-neoplastic condition.

9. The method of claim 8, wherein the pancreatic cancer or dysplasia is selected from the group consisting of pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma).

10. The method of claim 8, wherein the pre-cancerous pancreatic state is selected from the group consisting of mucinous cystadenoma, serous cystadenoma, islet cell tumor, mucinous duct ectasia, intraductal papillary mucinous Neoplasm, pancreatic intraepithelial neoplasia (PaniN grades 1-3), and solid and cystic papillary tumor of the pancreas.

11. The method of claim 8, wherein the non-neoplastic condition is selected from the group consisting of pancreatitis, pancreatic pseudocyst, mesothelial cyst, lymphoepithelial cyst of the pancreas, and ischemic necrosis of the pancreas.

12. The method of claim 1, wherein the other structural alterations in DNA are selected from the group consisting of gene amplification, gene translocation or rearrangement, and epigenetic modification of DNA by DNA methylation.

13. A method for diagnosing and/or determining the prognosis of a pancreatic anomaly in a patient suffering from pancreatic cysts comprising:
   a) performing molecular analysis of DNA from an aspirate from a patient pancreatic cyst comprising
      (i) performing an optical density analysis of the aspirate to determine DNA quantity;
      (ii) performing a quantitative PCR analysis ofthe aspirate to determine DNA quality;
      (iii) performing competitive template PCR to determine DNA quality; and
   b) performing mutation analysis of the DNA in the aspirate comprising:
      (i) determining the presence of one or more mutations in a tumor suppressor gene and/or the presence of a cancer related genetic marker;
      (ii) determining tumor suppressor gene loss of heterozygosity (LOH) by analyzing polymorphic microsatellites or other polymorphic markers linked to tumor suppressor genes with respect to their allelic balances;
      (iii) determining point mutations in the K-ras oncogene and/or point mutations in at least one other cancer-associated gene;
      (iv) determining other structural alterations in DNA;
      (v) determining the percentage of mutated DNA from steps b)(ii) and b)(iii); and
      (vi) determining the specific temporal sequence of mutation accumulation based on step v), and diagnosing and/or determining the prognosis of a pancreatic anomaly of the patient in need based on the results of steps a) and b).

14. The method of claim 13, wherein the pancreatic anomaly is a pancreatic cancer or dysplasia, pre-cancerous pancreatic state or non-neoplastic condition.

15. The method of claim 14, wherein the pancreatic cancer or dysplasia is selected from the group consisting of pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma).

16. The method of claim 14, wherein the pre-cancerous pancreatic state is selected from the group consisting of mucinous cystadenoma, serous cystadenoma, islet cell tumor, mucinous duct ectasia, intraductal papillary mucinous neoplasm, pancreatic intraepithelial neoplasia (PaniN grades 1-3), and solid and cystic papillary tumor of the pancreas.

17. The method of claim 14, wherein the non-neoplastic condition is selected from the group consisting of pancreatitis, pancreatic pseudocyst, mesothelial cyst, lymphoepithelial cyst of the pancreas, and ischemic necrosis of the pancreas.

18. A method for determining a course of treatment for a pancreatic anomaly in a patient suffering from pancreatic cysts comprising:
  a) performing molecular analysis of DNA from an aspirate from a patient pancreatic cyst comprising:
     (i) performing an optical density analysis of the aspirate to determine DNA quantity;
     (ii) performing a quantitative PCR analysis of the aspirate to determine DNA quality; and
     (iii) performing competitive template PCR to determine DNA quality; and
  b) performing mutation analysis of the DNA in the aspirate comprising:
     (i) determining the presence of mutations in a tumor suppressor gene and/or the presence of a cancer related genetic marker;
     (ii) determining tumor suppressor gene loss of heterozygosity (LOH) by catalyzing polymorphic microsatellites or other polymorphic markers linked to tumor suppressor genes with respect to their allelic balances;
     (iii) determining point mutations in the K-ras oncogene and/or point mutations in at least one other cancer-associated gene;
     (iv) determining other structural alterations in DNA;
     (v) determining the percentage of mutated DNA from steps b)(ii) and b)(iii); and
     (vi) determining the specific temporal sequence of mutation accumulation based on step v), wherein the results of steps a) and b) are used to determine a course of therapy for a patient suffering from a pancreatic anomaly.

19. The method of claim 18, wherein the pancreatic anomaly is a pancreatic cancer or dysplasia, pre-cancerous pancreatic state or non-neoplastic condition.

20. The method of claim 19, wherein:
  the pancreatic cancer or dysplasia is selected from the group consisting of pancreatic ductal adenocarcinoma, pancreatic acinar cell carcinoma, neuroendocrine cell carcinoma, sarcoma of the pancreas, metastatic cancer involving the pancreas, pancreaticoblastoma, and bile duct carcinoma (cholangiocarcinoma);
  the pre-cancerous pancreatic state is selected from the group consisting of mucinous cystadenoma, serous cystadenoma, islet cell tumor, mucinous duct ectasia, intraductal papillary mucinous neoplasm, pancreatic intraepithelial neoplasia (PanIN grades 1-3), and solid and cystic papillary tumor of the pancreas; and
  the non-neoplastic condition is selected from the group consisting of pancreatitis, pancreatic pseudocyst, mesothelial cyst, lymphoepithelial cyst of the pancreas, and ischemic necrosis of the pancreas.

\* \* \* \* \*